US011136539B2

(12) United States Patent
Sankai

(10) Patent No.: US 11,136,539 B2
(45) Date of Patent: Oct. 5, 2021

(54) FUNCTIONAL IMPROVEMENT EVALUATION APPARATUS AND NERVE CELL CULTURE APPARATUS OF MODEL ANIMALS

(71) Applicants: CYBERDYNE Inc., Tsukuba (JP); University of Tsukuba, Tsukuba (JP)

(72) Inventor: Yoshiyuki Sankai, Tsukuba (JP)

(73) Assignees: CYBERDYNE Inc., Tsukuba (JP); University of Tsukuba, Tsukuba (JP)

( * ) Notice: Subject to any disclaimer, the term of this patent is extended or adjusted under 35 U.S.C. 154(b) by 204 days.

(21) Appl. No.: 15/571,000

(22) PCT Filed: Apr. 26, 2016

(86) PCT No.: PCT/JP2016/063114
§ 371 (c)(1),
(2) Date: Sep. 20, 2018

(87) PCT Pub. No.: WO2016/178393
PCT Pub. Date: Nov. 10, 2016

(65) Prior Publication Data
US 2019/0017007 A1    Jan. 17, 2019

(30) Foreign Application Priority Data

May 1, 2015  (JP) .............................. JP2015-094288

(51) Int. Cl.
*C12M 3/00*     (2006.01)
*A01K 15/02*    (2006.01)
(Continued)

(52) U.S. Cl.
CPC ............. *C12M 21/08* (2013.01); *A01K 15/02* (2013.01); *A01K 15/027* (2013.01);
(Continued)

(58) Field of Classification Search
CPC ............. A01K 2267/0331; A01K 15/02; A01K 2267/03; A01K 15/027; A61B 5/1105;
(Continued)

(56) References Cited

U.S. PATENT DOCUMENTS 6,645,126 B1 *  11/2003  Martin ............... A63B 69/0059
                                                            482/3
2002/0157617 A1 *  10/2002  Reinkensmeyer ... A01K 15/027
                                                            119/728
(Continued)

FOREIGN PATENT DOCUMENTS

EP        2226006 A1     9/2010
JP     2004-147521 A     5/2004
(Continued)

OTHER PUBLICATIONS

International Search Report and Written Opinion for related PCT application No. PCT/JP2016/063114 dated Aug. 2, 2016, 6 pages.
(Continued)

*Primary Examiner* — Peter M Poon
*Assistant Examiner* — Jeffrey R Larsen
(74) *Attorney, Agent, or Firm* — Procopio, Cory, Hargreaves & Savitch LLP

(57) ABSTRACT

Proposed are a functional improvement evaluation apparatus and a nerve cell culture apparatus of model animals capable of performing feedback control, even to mammalian model animals, based on biosignals in the same manner has humans based on a relatively simple configuration. The present invention comprises a biosignal detection unit which is mounted on a central side above an intended in vivo site of a mammalian model animal and/or a peripheral side below an intended in vivo site of a mammalian model animal, and detects a biosignal resulting from a biological activity of the model animal, a control unit which causes a driving source (Continued)

to generate power according to an intent of the model animal based on the biosignal detected by the biosignal detection unit, and a motion transmission mechanism which is connected to a holding part for holding a foot of each leg of the model animal, and transmits the power of the driving source to the holding part so that the holding part swings at a same or approximate trajectory as a natural walking motion pattern of the model animal, and the control unit controls the power of the driving source based on a swing state of the holding part connected to the motion transmission mechanism.

6 Claims, 13 Drawing Sheets

(51) Int. Cl.
    *A61B 5/11*     (2006.01)
    *A61H 3/00*     (2006.01)
    *A63B 22/02*     (2006.01)
    *A01K 29/00*     (2006.01)
(52) U.S. Cl.
    CPC .......... *A61B 5/1105* (2013.01); *A61B 5/1128* (2013.01); *A61H 3/008* (2013.01); *A63B 22/0235* (2013.01); *C12M 3/00* (2013.01); *A01K 29/005* (2013.01)
(58) Field of Classification Search
    CPC . A61B 2503/40; A61B 5/1038; A61B 250/42; A61B 5/112; A61N 1/0551; A61N 1/36062; A61N 1/3605; A61N 1/36103; A63B 22/02; A63B 2202/0235; A63B 2208/14; A63B 1/0009
    USPC ........ 119/700; 482/54, 43, 69; 607/117, 2, 3
See application file for complete search history.

(56) References Cited

U.S. PATENT DOCUMENTS

| | | | | |
|---|---|---|---|---|
| 2004/0255344 | A1* | 12/2004 | Sakai | A01K 67/027 800/14 |
| 2013/0034905 | A1* | 2/2013 | Feng | C12N 5/0068 435/404 |
| 2014/0058299 | A1* | 2/2014 | Sankai | A61B 5/112 601/35 |
| 2014/0163640 | A1* | 6/2014 | Edgerton | A61N 1/36153 607/48 |
| 2014/0180361 | A1* | 6/2014 | Burdick | A61N 1/36007 607/49 |
| 2016/0279418 | A1* | 9/2016 | Courtine | A61N 1/0551 |

FOREIGN PATENT DOCUMENTS

| | | |
|---|---|---|
| JP | 2006-320221 A | 11/2006 |
| JP | 2008-264509 A | 11/2008 |
| JP | 2013-31425 A | 2/2013 |
| JP | 2013-94093 A | 5/2013 |
| JP | 2014-161587 A | 9/2014 |
| WO | 2012/118143 A1 | 9/2012 |

OTHER PUBLICATIONS

Extended European Search Report for related EP App No. 16789529.1 dated Nov. 26, 2018, 11 pgs.

\* cited by examiner

FIG. 12 (a)
FIG. 12 (b)
 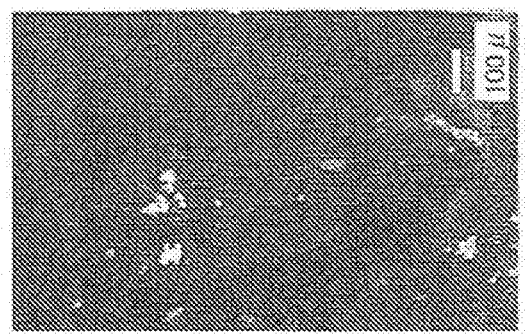
FIG.13
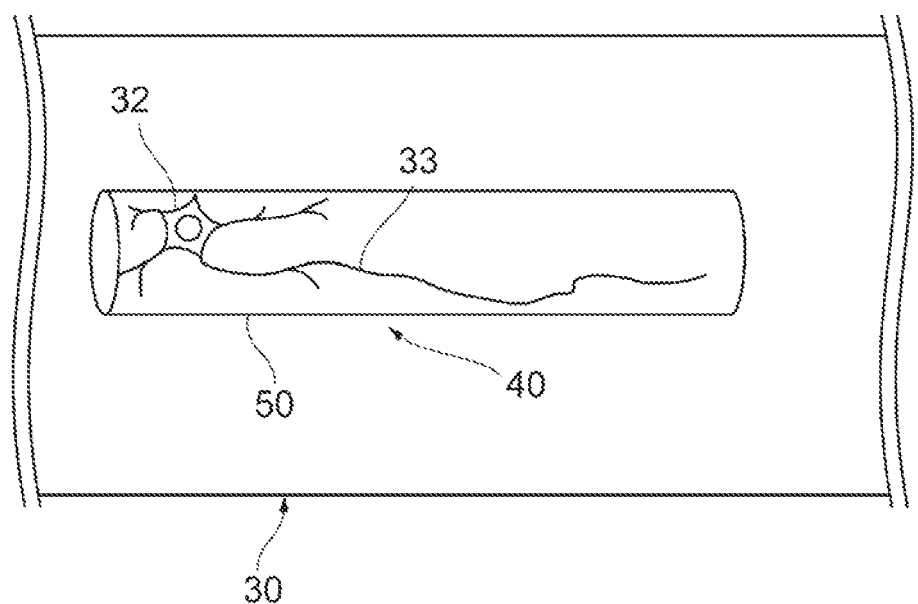

42

FUNCTIONAL IMPROVEMENT EVALUATION APPARATUS AND NERVE CELL CULTURE APPARATUS OF MODEL ANIMALS

TECHNICAL FIELD

The present invention relates to a functional improvement evaluation apparatus and a nerve cell culture apparatus of model animals, and, for instance, can be suitably applied to an evaluation apparatus for evaluating the physiological function and motor function of a rat pursuant to its walking motion.

BACKGROUND ART

Electrocardiograms, electroencephalograms, electro-oculograms and electromyograms that are acquired by measuring bioelectric potential signals such as cardiac potentials, brain waves, ocular potentials and muscle potentials are important biological information in comprehending the condition of test subjects and patients (hereinafter collectively referred to as "subjects") in medical practice.

For example, the primary cause of a functional disorder of the kinetic system is a cerebrovascular disorder such as cerebral apoplexy, and various motor function disorders appear depending on the symptom. In recent years, as a training system for performing the neuro rehabilitation of subjects suffering from a disease of the brain/nerve system, disclosed is a type for performing training to achieve the motor function recovery of subjects by using a body-worn motion assist device (for example, refer to PTL 1).

This body-worn motion assist device is configured to detect bioelectric potential signals that are generated when the subject moves his/her muscles, control the drive torque of the motor based on the detected bioelectric potential signals, and transmit the drive torque to the arms or legs of the subject.

Thus, even with a subject whose arm or leg is paralyzed, if the bioelectric potential signals can be detected from that subject, it is possible to effectively perform the neuro rehabilitation of the paralyzed arm or leg by moving the body-worn motion assist device based on the subject's intent.

CITATION LIST

Patent Literature

[PTL 1] Japanese Patent Application Publication No. 2008-264509

SUMMARY OF THE INVENTION

Problems to be Solved by the Invention

Meanwhile, in clarifying the pathogenic mechanism of a human disease and developing the treatment method and therapeutic drug thereof, animal experiments which use model animals exhibiting a disease state that resembles the human disease play an important role. While there is no particular limitation regarding these model animals so as long as they are generally used mammals, for instance, it is desirable to use rats, mice, hamsters or guinea pigs.

Even with the training system based on the bioelectric potential signals described above, it would be highly desirable to be able to clarify the pathogenic mechanism of a nerve or muscular disease by using model animals, and additionally develop the treatment method and therapeutic drug thereof.

Nevertheless, while model animals are common with humans with respect to the point that they are mammals, their body size is extremely small at several times smaller to approximately 1/200 times smaller in comparison to humans. In addition, functions against the mechanical load of the spine (vertebra connector) are completely different between model animals and humans. In other words, while the spine of humans is erect due to bipedal walking, the spine of most model animals is horizontal due to quadrupedal walking.

Due to the foregoing difference, an original and unique configuration is required because, with a simple design change of downsizing the body-worn motion assist device developed for humans, the transmission mechanism of the drive torque of the motor and the method of acquiring bioelectric potential signals will not be suitable for model animals.

Thus, there was a problem in that it was extremely difficult to apply a support system for humans based on bioelectric potential signals to small four-legged mammalian model animals merely based on an improved design.

The present invention was devised in view of the foregoing points, and an object of this invention is to propose a functional improvement evaluation apparatus and a nerve cell culture apparatus of model animals capable of performing feedback control, even to mammalian model animals, based on biosignals in the same manner has humans based on a relatively simple configuration.

Means to Solve the Problems

In order to solve the foregoing problems, the present invention provides a functional improvement evaluation apparatus of a model animal, comprising: a biosignal detection unit which is mounted on a central side above an intended in vivo site of a mammalian model animal and/or a peripheral side below an intended in vivo site of a mammalian model animal, and detects a biosignal resulting from a biological activity of the model animal; a control unit which causes a driving source to generate power according to an intent of the model animal based on the biosignal detected by the biosignal detection unit; and a motion transmission mechanism which is connected to a holding part for holding a foot of each leg of the model animal, and transmits the power of the driving source to the holding part so that the holding part swings at a same or approximate trajectory as a natural walking motion pattern of the model animal, wherein the control unit controls the power of the driving source based on a swing state of the holding part connected to the motion transmission mechanism.

According to the foregoing configuration, it is possible to combine the leg anatomy of the model animal and the transmission mechanism of the motion transmission mechanism and connect the end effector of the power of the driving source to the feet of the model animal, and thereby assist the walking motion of the model animal. Consequently, it is possible to feed back the autonomous control for realizing the optional control and walking motion according to the model animal's intent, without having to cause the model animal to wear the driving source as an external skeleton, based on the biosignals that are detected with the in vivo site (damaged or ruptured area of the spinal cord or cranial nerve) of the model animal as the reference.

Moreover, the present invention further comprises a biostimulation application unit which is provided in substitute for the biosignal detection unit or provided at a same site as the biosignal detection unit, and applies a physical stimulation to the model animal based on a signal from the control unit, and the control unit generates a signal to be sent to the biostimulation application unit based on the biosignal. Consequently, even in cases where the in vivo site (for instance, the spinal cord) is ruptured, it is possible to move parts or acquire sensations on a peripheral side that is more peripheral than the ruptured area.

Moreover, the present invention further comprises a monitoring/measurement unit which, with a catheter inserted into a bladder of the model animal, monitors an activity of a bladder and/or a urethra via the catheter based on the biosignal detected pursuant to a walking motion of the model animal. Consequently, the monitoring result can be used for clarifying the functional improvement of a bladder/excretory disorder.

Moreover, the present invention further comprises a treadmill which causes a walking belt to move in a circular motion according to a rotation of rollers, the motion transmission mechanism positions the holding part for holding a foot of each leg of the model animal so that the holding part can come into contact with the walking belt, and the control unit controls a moving speed of the walking belt according to a walking motion of the model animal. Consequently, when the model animal engages in an actual walking motion, it is possible to offer a sensation to the model animal of naturally stepping on the walking belt.

Moreover, the present invention further comprises a centroid position detection unit which is provided on the holding part for holding a foot of each leg of the model animal, and detects a centroid position according to a walking motion of the model animal, and a relief device which lifts the model animal in a freely elevatable manner, and relieves a load on a foot of each leg of the model animal, and the control unit controls the relief by the relief device based on the centroid position of the model animal. Consequently, it is possible to detect the centroid position from the floor reaction on the walking belt and enable the model animal to engage in a natural walking motion even when the legs of the model animal are weak.

The present invention additionally provides a nerve cell culture apparatus, comprising: an implant module which is implanted in an intended in vivo site of a mammalian model animal, and which places nerve cells, and a guide member for guiding neurites of the nerve cells in an elongation direction, on a culture substrate; a biosignal detection unit which is mounted on a central side above the implant module and/or a peripheral side below the implant module, and detects a biosignal resulting from a biological activity of the model animal; a control unit which causes a driving source to generate power according to an intent of the model animal based on the biosignal detected by the biosignal detection unit; and a motion transmission mechanism which is connected to a holding part for holding a foot of each leg of the model animal, and transmits the power of the driving source to the holding part so that the holding part swings at a same or approximate trajectory as a natural walking motion pattern of the model animal.

According to the foregoing configuration, it is possible to combine the leg anatomy of the model animal and the transmission mechanism of the motion transmission mechanism and connect the end effector of the power of the driving source to the paws of the model animal, and thereby assist the walking motion of the model animal. Consequently, it is possible to culture nerve cells in the implant module implanted in the relevant site, without having to cause the model animal to wear the driving source as an external skeleton, based on the biosignals that are detected with the in vivo site (damaged or ruptured area of the spinal cord or cranial nerve) of the model animal as the reference.

Advantageous Effects of the Invention

According to the present invention, it is possible to perform optional and autonomous feedback control, even to mammalian model animals, based on biosignals in the same manner has humans based on a relatively simple configuration, and thereby build an evaluation apparatus for improving the motor function and physiological function using a model animal.

BRIEF DESCRIPTION OF DRAWINGS

FIGS. 12(a)-12(b) is a diagram showing another example of a phase-contrast micrograph and a fluorescence micrograph of the nerve cells according to this embodiment.

FIG. 13 is a conceptual diagram explaining a first modified example of the culture method of nerve cells according to this embodiment.

DESCRIPTION OF EMBODIMENTS

Figure 1:
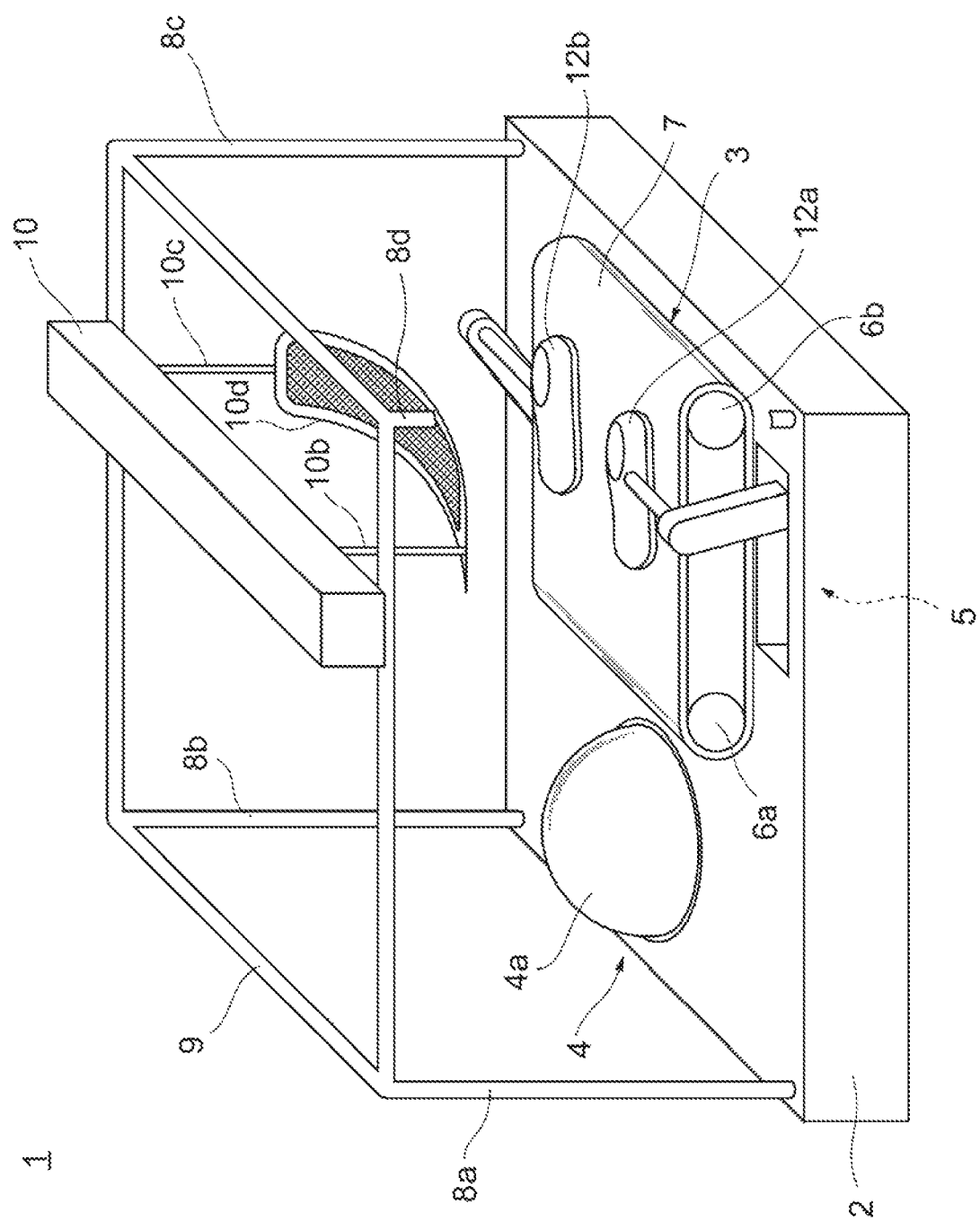
FIG. 1 is an external perspective view of a functional improvement evaluation apparatus for evaluating the functional improvement of a rat according to an embodiment of the present invention.

An embodiment of the present invention is now explained in detail with reference to the appended drawings.

(1) Principle of Functional Improvement Evaluation Method

With the functional improvement evaluation method of the present invention, a walking motion assist device described later is used, while causing a rat with a spinal cord injury to walk on a treadmill, to detect bioelectric potential signals generated when the rat moves its muscles, and assist the walking motion of the rat based on the detected bioelectric potential signals.

Thus, even with a rat with a spinal cord injury whose legs are paralyzed, so as long as bioelectric potential signals can be detected from the rat, it is possible to operate the motion assist device based on the rat's own intent and effectively perform the neuro rehabilitation of the paralyzed legs.

Moreover, in addition to cases where the rat's spinal cord is damaged, even when the rat's spinal cord is ruptured and nerves do not reach its legs, it is possible to assist the rat's walking motion using the motion assist device by implanting a potential detection sensor (electrode) above the ruptured area and detecting the biopotential (nerve action potential) signals based on commands from the brain.

Specifically, muscle spindles sense the expansion and contraction of skeletal muscles, and are configured from muscles referred to as intrafusal muscle fibers, several sensory nerve endings wrapped around the intrafusal muscle fibers, and gamma motor neurons which are responsible for the motor innervation of the intrafusal muscle fibers. Moreover, the muscle spindles are interspersed between, and arranged in parallel with, the skeletal muscle fibers, and exist in large quantities in muscles of eyeballs, fingers and the like which require finely controlled movements. When the intrafusal muscle fibers expand pursuant to the skeletal muscles, the sensory nerve endings wrapped around the intrafusal muscle fibers are stimulated and generate proprioceptive impulses, and nerve action potential signals from the muscle spindles are thereby detected.

Biosignals (for instance, bioelectric potential signals) that are fed back from the peripheral system to the central nervous system may be detected when the rat moves its own body parts or reacts to external stimuli. Biosignals that pass through the central nervous system including the brain, and the neural circuit which is connected to the peripheral system via the spinal cord and motor nerve, can be measured from both the direction from the central nervous system toward the peripheral system, and the direction from the peripheral system toward the central nervous system.

It is thereby possible to confirm whether the signals transmitted from the brain have correctly reached the peripheral system, and whether information from the peripheral system has been properly fed back to the brain. By assisting the rat's walking motion as described above, it is possible to artificially build a nerve system loop and promote the in vivo/in vitro interactive bio feedback between the brain/nerve system (central nervous system) and the musculoskeletal system (peripheral system/body), and thereby establish a technology for promoting functional improvement.

Incidentally, the sensor (biosignal detection unit) to be implanted in a rat is, for example, a micro sensor (micro electrode) having a silicone substrate and a metal material formed on the silicone substrate, and, as the metal material, used is a corrosive-resistant noble metal such as gold or platinum or the alloys thereof. A plurality of sensors are provided, and include a sensor for detecting the ground potential and a sensor for detecting the reference potential.

As a result of using a cylindrical or clamp-shaped sensor having a hollow space (through hole) in which nerve fibers are placed as the foregoing sensors and providing the sensor part (metal part) on the lateral face of the through hole, the electrical contact between the sensor and the nerve fiber becomes stabilized, and the nerve action potential can be stably detected from the nerve fibers. Moreover, a needle-type sensor may also be used as the foregoing sensor, and pierced into the nerve fibers.

The wiring includes a conductor made from copper or gold, and an insulative resin material which covers the conductor. As the insulative resin material, a flexible material with high biocompatibility such as silicone resin or polyurethane resin may be used.

The sensors are implanted in vivo through surgery. For example, the sensors are arranged to come into contact with the axial fibers or dendrites of the central nervous system or the peripheral system.

While the foregoing embodiment explained a case where a sensor (biosignal detection unit) detects the nerve action potential, the sensor may also be used to apply electrostimulation to biotissues. Moreover, the walking motion assist device may additionally comprise a sensor for detecting the nerve action potential, and a sensor for applying electrostimulation to biotissues. For example, the potential detection sensor detects the nerve action potential in a path (for example, the spinal cord ascending tract) which ascends toward the upper nerve center (for example, the brain). The electrostimulation sensor (biostimulation application unit) applies electrostimulation in a path (for example, the spinal cord descending tract) which descends from the upper nerve center. Consequently, even in cases where the spinal cord is ruptured, it is possible to move parts or acquire sensations on a side that is lower than the ruptured area. It is also possible to determine the electrostimulation to be applied to the biotissues based on the nerve action potential detected in the ascending tract, and thereby apply electrostimulation from the stimulation sensor.

Furthermore, there is no particular limitation regarding the model animals that can be used in the present invention as long as they are mammals that are generally used as model animals in relation to human diseases, and, in addition to rats, for instance, mice, hamsters, and guinea pigs may also be used.

(2) Overall Configuration of Functional Improvement Evaluation Apparatus

FIG. 1 is an external perspective view of a functional improvement evaluation apparatus 1 for evaluating the functional improvement of a rat according to an embodiment of the present invention. With the functional improvement evaluation apparatus 1, a treadmill 3 and a spherical rolling part 4 are juxtaposed on a base 2, and a walking motion assist device 5 (FIG. 3) is built in below the base 2 with the treadmill 3 as a reference.

The treadmill 3 includes a walking belt 7 which moves in a circular motion according to the rotation of rollers 6a, 6b. The walking belt 7 is arranged horizontally. A motor 3a (FIG. 3) can rotate the rollers 6a, 6b via a transmission mechanism. The circulation speed of the walking belt 7 can be changed by changing the rotation speed of the rollers 6a, 6b. Furthermore, the walking belt 7 can be inclined in the front-back direction like a slope, and the load of the walking motion can be increased by causing the slope to become steep, and the load of the walking motion can be reduced by causing the slope to be more horizontal.

Moreover, with the spherical rolling part 4, a shaft bearing configured from a support ball or a ball bearing is placed at three locations in a holding space (not shown) formed in the base 2, and a hard ball 4a is mounted so that it can smoothly and freely rotate in any direction, in a three-dimensional manner, based on the three-point mounting of the shaft bearings.

Furthermore, support columns 8a to 8d are erected at each of the four corners on the upper face of the base 2, and a support frame 9 is connected to the upper end of the support columns 8a to 8d so that the overall apparatus configures a substantial rectangular parallelepiped frame body. A relief device 10 is placed across the support frame 9, and is able to freely slide and move along the juxtaposed direction of the treadmill 3 and the spherical rolling element 4.

The relief device 10 includes a servo motor 10a (FIG. 3) which is conductively connected with the walking motion assist device 5, and, for instance, is connected to one end of suspending harnesses 10b, 10c. A hammock-shaped holding part 10d for enwrapping and holding the rat's body is mounted on the other end of the harnesses 10b, 10c.

The relief of the load on the rat's paws is determined depending on the extent that the servo motor 10a lifts the harnesses 10b, 10c. The higher the harnesses 10b, 10c are lifted, the relief will increase, and the load on the rat's paws will decrease.

Moreover, the functional improvement evaluation apparatus 1 is additionally provided with an input unit 11 (FIG. 3) for adjusting the rotation speed of the rollers 6a, 6b based on the motor 3a in the treadmill 3, and the relief provided by the relief device 10. By using the input unit 11, the outside operator can adjust the speed of the walking belt 7 and the load on a pair of special-purpose shoes 12a, 12b. For example, the input unit 11 can be used to set the speed of the walking belt 7 to be roughly the same as the walking speed of rats.

Figure 2:
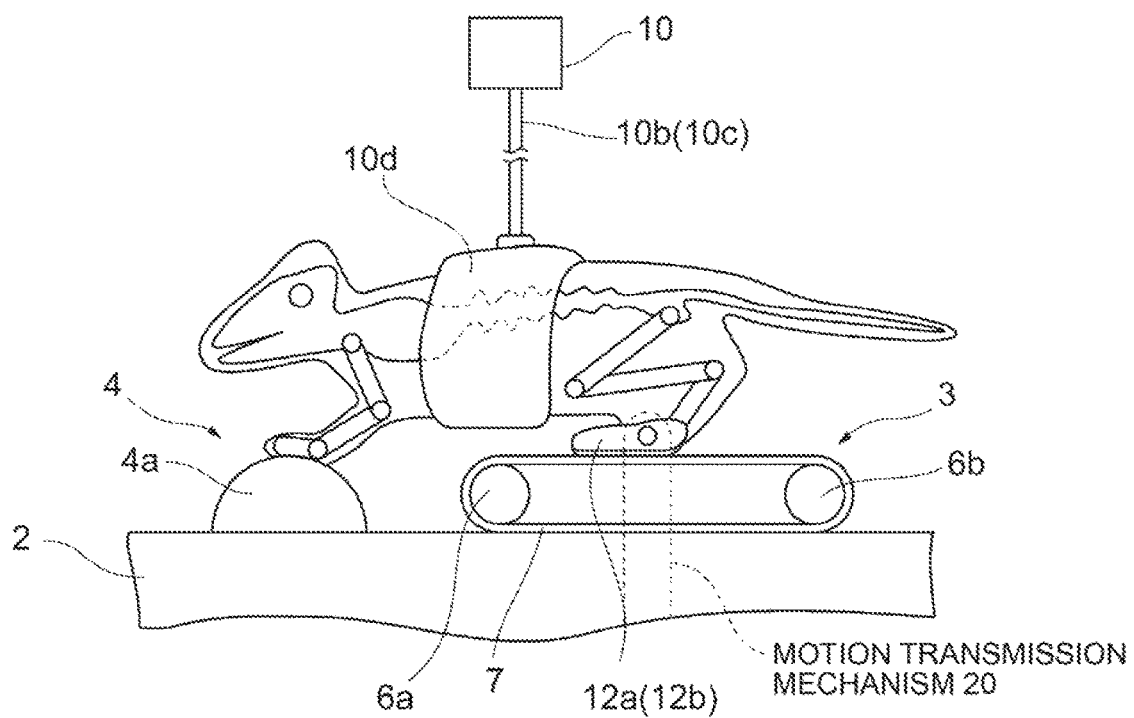
FIG. 2 is a conceptual diagram explaining a state where a rat has been set in the functional improvement evaluation apparatus according to this embodiment.

FIG. 2 shows a case where a rat is set in the functional improvement evaluation apparatus 1 configured as described above. Foremost, while holding the rat's body with the hammock-shaped holding part 10d, the special-purpose shoes 12a, 12b are each placed on a pair of paws of the rat. Next, while using the relief device 10 to adjust the load of the pair of special-purpose shoes 12a, 12b on the walking belt 7 of the treadmill 3, the paws of the rat's pair of front legs are caused to come into contact with the surface of the hard ball 4a of the spherical rolling part 4.

In this state, when an item of interest (favorite feed or the like) or a video monitor is placed in front of the rat within its visual field and the walking belt 7 of the treadmill 3 is moved at an optimal speed, the rat will independently start its walking motion, and, simultaneously with rotating the hard ball 4a of the spherical rolling part 4 in its intended direction with the paws of the pair of front legs, take one step at a time on the walking belt 7 of the treadmill 3 with the special-purpose shoes 12a, 12b worn on the paws of the pair of back legs.

Furthermore, the functional improvement evaluation apparatus 1 detects the bioelectric potential signals that are generated when the rat moves its muscles, controls the drive torque from the driving source 21 (FIG. 3) based on the detected bioelectric potential signals, and thereby transmits the drive torque to the pair of special-purpose shoes 12a, 12b and applies assist force (power) to each of the rat's legs.

Figure 3:
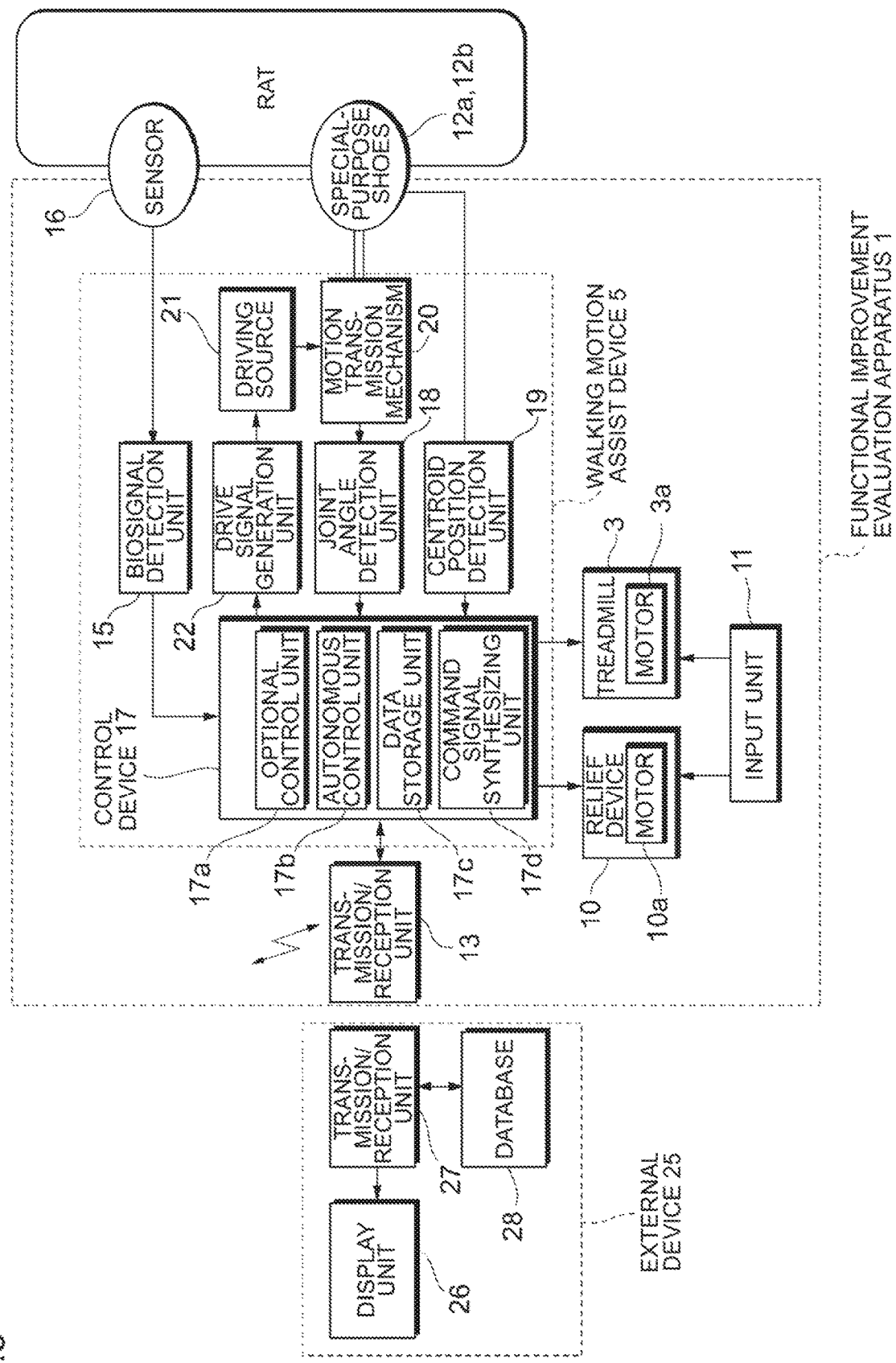
FIG. 3 is a block diagram showing a configuration of the control system of the functional improvement evaluation apparatus according to this embodiment.

(3) Configuration of Control System of Functional Improvement Evaluation Apparatus FIG. 3 is a block diagram showing a configuration of the control system of the functional improvement evaluation apparatus 1 according to this embodiment. The functional improvement evaluation apparatus 1 comprises a walking motion assist device 5, a relief device 10, a treadmill 3, and a transmission/reception unit 13.

In the walking motion assist device 5, a biosignal detection unit 15 detects bioelectric potential signals from a sensor 16, which is implanted in a rat in vivo, when the rat moves its muscles around its joints. For example, in cases where the rat's spinal cord is ruptured or damaged and the nerves do not sufficiently reach its legs, the sensor 16 is implanted above the ruptured area or the damaged area (on the side that is closer to the brain), and the nerve action potential is detected from the nerve fibers.

The biosignal detection unit 15 sends the bioelectric potential signals detected by the sensor 16 to a control device 17.

A joint angle detection unit 18 detects the swing angle of an end effector of a motion transmission mechanism 20 (FIG. 6) according to the rat's movement as the joint angle of the rat's legs, and outputs the detected swing angle to the control device 17. An angle sensor (not shown) is used as the joint angle detection unit 18. The angle sensor is configured, for example, from a rotary encoder which counts the number of pulses proportional to the swing angle of the end effector of the motion transmission mechanism 20, and outputs, as a sensor output, electric signals corresponding to the number of pulses according to the swing angle. The angle sensor specifically detects the swing angle of the special-purpose shoes 12a, 12b as the end effectors of the motion transmission mechanism which is connected to the output axis of the driving source.

A centroid position detection unit 19 detects a centroid position according to the rat's movement, and outputs the detected centroid position to the control device 17. The control device 17 includes an optional control unit 17a, an autonomous control unit 17b, a data storage unit 17c and a command signal synthesizing unit 17d. The optional control unit 17a uses the bioelectric potential signals detected by the biosignal detection unit 15, and generates optional command signals for causing a driving source 21, which is configured from a servo motor, to generate power according to the rat's intent via the motion transmission mechanism 20.

The data storage unit 17c stores, in a reference parameter database, tasks of the rat's walking motion, and an assist parameter for assisting the rat's movement according to the task. Moreover, the data storage unit 17c temporarily stores the bioelectric potential signals detected by the biosignal detection unit 15.

Upon analyzing the general walking motion of rats, it can be understood that the typical movement pattern, such as the angle of the respective joints and the movement of the centroid, is predetermined. Thus, the displacement of typical joint angles and the status of shift in the centroid are empirically obtained in relation to the rat's walking motion, and stored in the reference parameter database. Furthermore, rats have different walking patterns depending on their body size, muscle condition, and walking speed. The proper movement pattern will differ depending on the degree of disorder or the progress of rehabilitation of the target rat. Thus, the corresponding assist pattern will differ even if it is the same task.

The autonomous control unit 17b compares the parameters representing the rat's movement such as the joint angles detected by the joint angle detection unit 18 and the centroid position detected by the centroid position detection unit 19, and the reference parameters stored in the data storage unit 17c, identifies the task of the rat's movement and thereafter selects the optimal assist pattern corresponding to the task, and thereby generates autonomous command signals for causing the driving source 21 to generate power according to the assist pattern.

The command signal synthesizing unit 17d synthesizes the optional command signals generated by the optional control unit 17a and the autonomous command signals generated by the autonomous control unit 17b, and outputs the synthesized command signals to a drive signal generation unit 22. The command signal synthesizing unit 17d includes a waveform for causing the driving source 21 to generate power obtained by synthesizing power based on optional control which changes from the start to end of the movement, and power based on autonomous control.

The drive signal generation unit 22 drives the driving source 21 by generating drive signals (drive current) according to the synthesized command signals and supplying the generated drive signals (drive current) to the driving source 21. The driving source 21 applies assist force (power) according to the drive signals, via the motion transmission mechanism 20, to each of the rat's legs with the pair of special-purpose shoes 12a, 12b as the medium.

A transmission/reception unit 13 is a communication device capable of transmission and reception based on a short-range wireless communication technology such as Bluetooth (Registered Trademark) serial communication. The transmission/reception unit 13 modulates, under the control of the control device 17, the reference parameters stored in the data storage unit 17c, the parameters representing the status of the rat's movement such as the joint angles detected by the joint angle detection unit 18 and the centroid position detected by the centroid position detection unit 19, and the bioelectric potential signals detected by the biosignal detection unit 15 into a predetermined transmission method, and sends the same to an external device 25 via an antenna.

The external device 25 is, for example, a diagnostic computer, and creates electrocardiograms and electroencephalograms and displays them on a display unit 26, uses a transmission/reception unit 27 to receive the various types of data sent from the functional improvement evaluation apparatus 1, and stores the received data in a database 28. Consequently, the external device 25 is able to constantly monitor the rat's kinetic state and physiological state, as well as manage data in a time series while accumulating such data in the database 28.

As described above, the functional improvement evaluation apparatus 1 applies assist force to the rat based on the walking motion assist device 5 and assists the rat's walking motion while stabilizing the rat's position by suspending the rat with the relief device 10. The control device 17 of the walking motion assist device 5 can control the speed of the walking belt 7 of the treadmill 3 based on the rat's walking speed, as well as control the relief of the relief device 10 based on the rat's centroid position or the leaning of the rat's body. Thus, even in cases where the independent movement of the rat's legs is difficult, the rat can safely perform its walking motion without having to worry about falling down or straying outside the walking belt 7.

(4) Configuration of Walking Motion Control Device

The walking motion assist device 5 detects the bioelectric potential signal that are generated when the rat moves its leg muscles, controls the drive torque of the driving source 21 based on the detected bioelectric potential signals, and thereby assists the rat's walking motion via the motion transmission mechanism 20.

The motion transmission mechanism 20 includes an articulated link mechanism which connects an output axis of a pair of driving sources 21 configured from a servo motor and the special-purpose shoes 12a, 12b to be worn by each of the rat's paws, and converts the rotational motion of the output axis of the driving sources 21 into a swing motion of a pseudo straight line to match the walking pattern of the rat's paws.

In the present invention, the pair of driving sources 21 is not mounted directly on each of the rat's legs, and is mounted via the motion transmission mechanism 20, and power is applied only to the special-purpose shoes 12a, 12b mounted on the rat's paws.

This is because it is extremely difficult to design and mount servo motors as the driving sources 21 in a size which matches the rat's legs, and also because the rotational motion of the output axis of the driving sources 21 needs to be converted into a pseudo linear motion. Furthermore, the reason why the present invention is feasible is because a rat's gait (repetitive pattern of the leg movement focused on timing) based on the rat's leg anatomy is basically a repetition of a fixed pattern, and is extremely simple in comparison a human's gait based on the skeleton of the lower limb.

Figure 4:
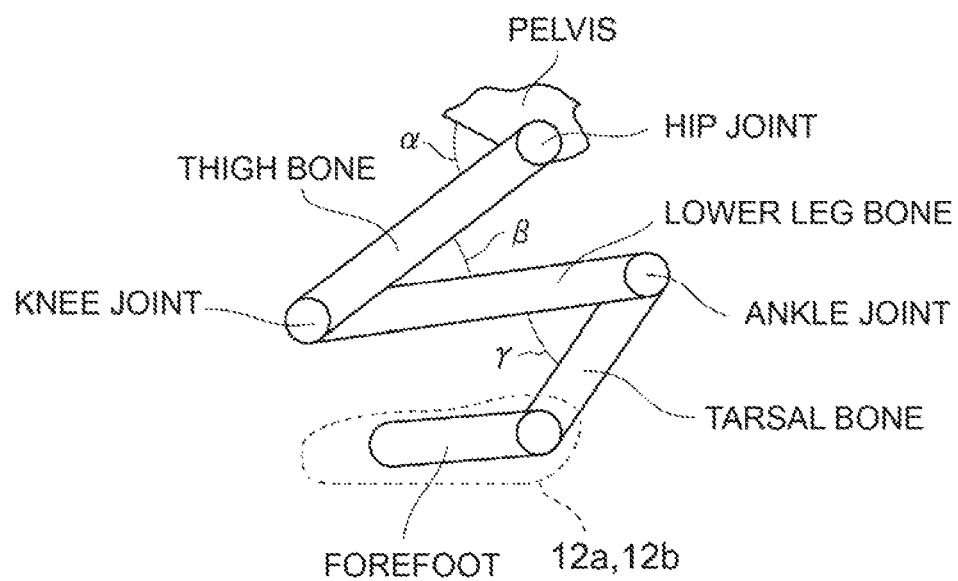
FIG. 4 is a conceptual diagram showing a functional configuration of the leg anatomy of a rat according to this embodiment.

As shown in FIG. 4, the leg of a rat is configured from a thigh bone, a lower leg bone, and a tarsal bone, and a range of motion (rotation angle $\alpha$) of a hip joint of a pelvis and a femoral region, a range of motion (rotation angle $\beta$) of a knee joint of a femoral region and a leg region, and a range of motion (rotation angle $\gamma$) of an ankle joint of a leg region and a tarsal bone are each substantially limited to be within a predetermined range during the gait.

In other words, with a rat's gait, because the position and motion of the legs substantially fall within a predetermined pattern, there is no need to drive both the hip joint and the knee joint as in humans, and the overall legs can be led to perform a walking motion so as long as the rat's paws are swung in a pattern that matches the rat's walking motion.

In effect, the pair of special-purpose shoes 12a, 12b is connected as the end effector of the power transmission in the motion transmission mechanism 20, and can be mounted on each of the rat's paws. Moreover, the special-purpose shoes 12a, 12b are positioned in the motion transmission mechanism 20 so as to engage in a swing motion of a pseudo straight line along the surface of the walking belt 7 with the treadmill 3 as a reference.

Furthermore, the pair of special-purpose shoes 12a, 12b is provided with a centroid sensor (not shown) such as a strain sensor (strain gauge) on the sole to measure the load on the underside of the rat's paws, and detect the movement of the centroid position based on changes in the measured load.

The motion transmission mechanism 20 is a mechanism for converting the rotational motion of the driving source 21 into a pseudo linear motion, and, for instance, comprises an articulated link mechanism having a degree of freedom of 1 and includes a four-joint link mechanism.

Figure 5:
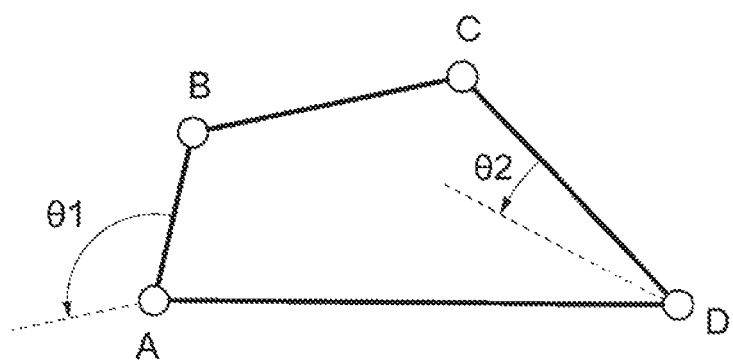
FIG. 5 is a conceptual diagram showing a four-joint link mechanism according to this embodiment.

Generally speaking, with a four-joint link mechanism, as shown in FIG. 5, one joint among the four joints of ABCD is fixed, when a link AB is connected to a driving source at a joint A and engaged in a rotational motion, the length of the link bars has a relation of AB<BC<CD<AD, and, if a link bar CD rotates θ2 degrees as a result of a link bar AB rotating θ1 degrees, then the relationship of θ1>θ2 is established. In other words, this can be utilized when moving a large object with a small power.

Figure 6:
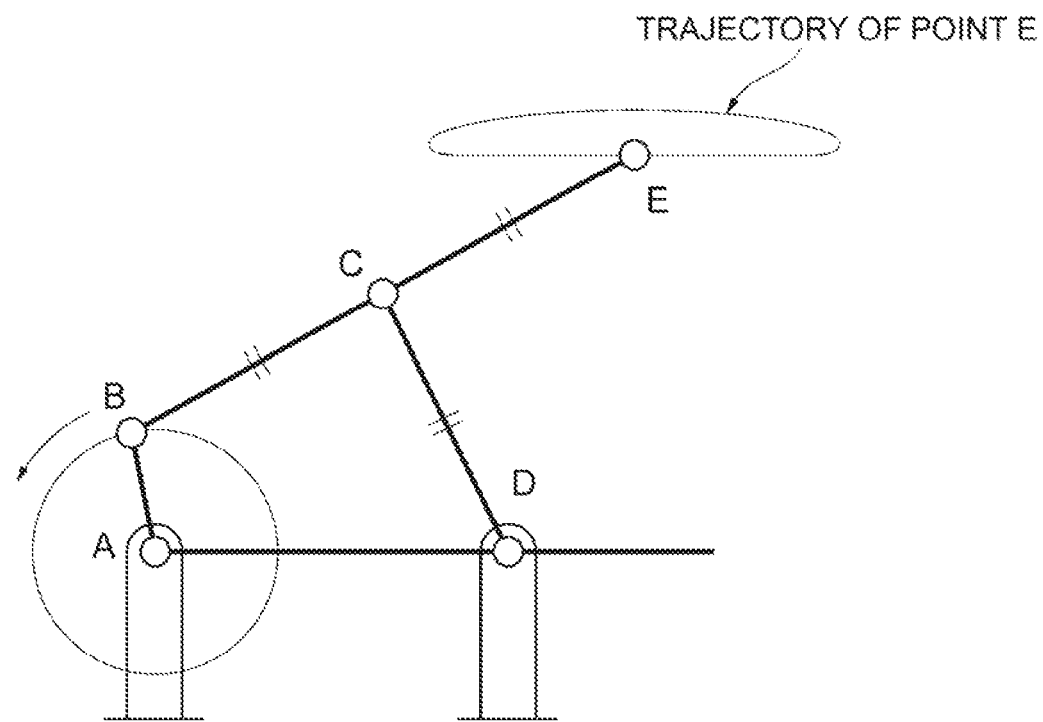
FIG. 6 is a conceptual diagram explaining Chebyshev's first approximate linear motion mechanism according to this embodiment.

As the articulated link mechanism in the present invention, used is a four-joint link mechanism having a degree of freedom of 1 which includes, for example, so-called Chebyshev's first approximate linear motion mechanism. As shown in FIG. 6, let it be assumed that point A and point D are fixed, and point B can rotate around point A. Furthermore, when point E exists on an extension of link bar BC, let it be assumed that the relational expression of Formula (1) and Formula (2) below has been established.

[Math 1]

$$AD=2AB \qquad (1)$$

[Math 2]

$$BC=CD=CE=2.5AB \qquad (2)$$

When point B engages in a circular motion under the conditions of foregoing Formula (1) and Formula (2), as shown in FIG. 6, a part of the trajectory of point E will become an approximate straight line. Note that, while not shown, as another mechanism for converting the rotational motion of the driving sources 21 into a pseudo linear motion, a compound four-joint link mechanism such as a so-called Theo Jansen mechanism may also be applied.

Here, as pre-processing, the movement of the rat's paws pursuant to the walking motion is measured by mounting a marker on the rat's paws and measuring the rat's movement of walking on the treadmill 3 via motion capture using a camera. Lissajous's figure (figure that is drawn upon combining the simple harmonic motion of two directions that are perpendicular to each other), which is a visualization of the two-dimensional movement of the rat's paws, is calculated in advance based on the movement analysis of the rat's paws.

In the motion transmission mechanism 20, the number of links of the articulated link mechanism including the four-joint link mechanism, length of the respective links, and positioning of the respective joints are adjusted to be within a range that maintains a degree of freedom of 1 so that the pair of special-purpose shoes 12a, 12b as the end effectors moves in a circular motion while drawing the intended Lissajous's figure.

Accordingly, by connecting the output axis of the pair of driving sources 21 to each of the corresponding special-purpose shoes 12a, 12b via the motion transmission mechanism 20, the walking motion assist device 5 realizes a movement of walking on the treadmill 3 while drawing a trajectory that is similar to the trajectory of the rat's paws.

Note that, while the foregoing embodiment explained a case where the articulated link mechanism of the present invention converts the rotational motion of the driving source 21 into a pseudo linear motion, the present invention is not limited thereto, and the rotational motion of the driving source 21 may also be converted into a true linear motion.

Figure 7:
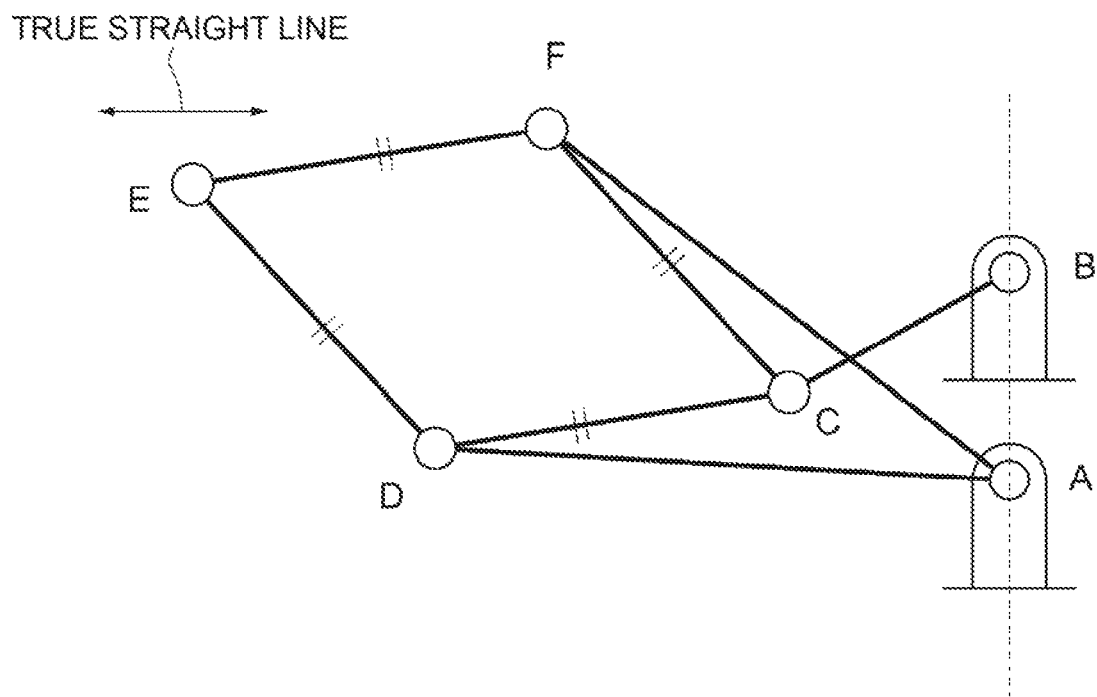
FIG. 7 is a conceptual diagram explaining the Paucellier mechanism according to another embodiment.

For example, a case of using a four-joint link mechanism having a degree of freedom of 1 and which includes a so-called Paucellier mechanism is shown in FIG. 7. In FIG. 7, let it be assumed that point A and point B are fixed, and the rotational motion of the driving sources 21 is transmitted via a predetermined crank mechanism (not shown) so as to swing point C with point B as a reference. Furthermore, let it be assumed that the relational expression of Formula (3) to Formula (5) below has been established.

[Math 3]

$$CD=DE=EF=FC \qquad (3)$$

[Math 4]

$$AD=AF \qquad (4)$$

[Math 5]

$$AB=BC \qquad (5)$$

When point C engages in a swing motion under the conditions of foregoing Formula (3) to Formula (5), as shown in FIG. 7, point E will engage in a linear reciprocating motion in a direction that is perpendicular to segment AB. Note that, while not shown, as another mechanism for converting the rotational motion or swing motion of the driving sources 21 into a true linear motion, a so-called Scotch yoke mechanism may also be applied.

Accordingly, various types of mechanisms may be applied as the motion transmission mechanism 20 so as long as the mechanism can convert all or a part of the rotational motion of the driving source 21 into a pseudo linear motion or a true linear motion, and in particular a mechanism including an articulated link mechanism having a degree of freedom of 1 is desirable from the perspective of structural design.

(5) Target-Based Functional Improvement Evaluation Method According to the Present Invention (5-1) Motor Function Improvement Evaluation Method In this embodiment, when the rat's spinal cord is damaged or ruptured (when the rat's spinal cord is intentionally damaged or ruptured for an evaluation experiment), by implanting a sensor 16 on the side of the nerve center (brain) that is above the damaged or ruptured area and detecting the biosignals (nerve action potentials) based on commands from the brain while causing the rat with a spinal cord injury to walk on the treadmill 3, the rat's walking motion is assisted.

In the present invention, bioelectric potential signals are signals resulting from the rat's biological activity, and are not limited to nerve action potential signals. Bioelectric potential signals are signals that can be measured from the rat's body and which change through time. Specifically, bioelectric potential signals include, for example, muscle potential signals and neural transmission signals, brain waves, cardiac potentials, potentials arising from motion artifacts, potentials arising from biochemical reactions, vibrations such as pulse waves arising from heart beats, and signals arising from biological activities.

As another embodiment, without limitation the side that is above the damaged or ruptured area of the rat's spinal cord, it is also possible to implant a potential detection sensor (electrode) on a side that is below the damaged or ruptured area of the rat's spinal cord, and detect the biosignals (for example, bioelectric potential signals) that are fed back from the peripheral system to the central nervous system when the rat engages in a walking motion. Bioelectric potential signals that pass through the central nervous system including the brain, and the neural circuit which is connected to the peripheral system via the spinal cord and motor nerve, can be measured from both the direction from the central nervous system toward the peripheral system, and the direction from the peripheral system toward the central nervous system. It is thereby possible to confirm whether the signals transmitted from the brain have correctly reached the peripheral system, and whether information from the peripheral system has been properly fed back to the brain.

Furthermore, as another embodiment, while a case of the potential detection sensor 16 detecting the nerve action potential has been explained, it is also possible to provide an electrostimulation sensor for applying electrostimulation to biotissues in substitute for, or integrally with, the potential detection sensor 16. For example, the potential detection sensor detects the nerve action potential in a path (for example, the spinal cord ascending tract) which ascends toward the upper nerve center (brain). The electrostimulation sensor applies electrostimulation in a path (for example, the spinal cord descending tract) which descends from the upper nerve center. Consequently, even in cases where the spinal cord is ruptured, it is possible to move parts or acquire sensations on a side that is lower than the ruptured area. It is also possible to determine the electrostimulation to be applied to the biotissues based on the nerve action potential detected in the ascending tract, and thereby apply electrostimulation from the electrostimulation sensor.

While the foregoing embodiment explained a case of applying an electrostimulation sensor as the biostimulation application unit that is provided in substitute for, or integrally with, the sensor (biosignal detection unit), the present invention is not limited thereto, and, so as long as physical stimulation can be applied to the model animal, in addition to electrical stimulation, various other physical stimulation application means capable of applying vibration-based mechanical stimulation, thermal stimulation based on temperature change, magnetic stimulation or ultrasonic stimulation may also be broadly applied.

As yet another embodiment, while the foregoing embodiment explained a case of applying the damaged or ruptured area of the spinal cord as the rat's intended in vivo site, the present invention is not limited thereto, and the damaged or ruptured area of the rat's cranial nerve may also be applied as the in vivo site. In the foregoing case, the damaged or ruptured area due to cerebral infarction or the like will be the area or location of a hole within the cranial nerve, and two or more sensors (not shown) are implanted so as to sandwich the foregoing area or location.

(5-2) Physiological Function Improvement Evaluation Method

Furthermore, in addition to applying the functional improvement evaluation apparatus 1 of the present invention to the motor function improvement of rats, it may also be applied to the physiological function improvement of a bladder/excretory disorder or the like.

A bladder is a bag that is configured from muscular tissues, and adjusts urine collection and urination by controlling the bladder detrusor and the urethral sphincter through a complex nerve system, but when a spinal cord injury occurs, irrespective of the height of the damaged area, it is known that the balance of the tension or relaxation of the bladder detrusor and the urethral sphincter becomes lost, and results in a urination disorder.

Thus, with a catheter (not shown) inserted into the rat's bladder, the functional improvement of the bladder/excretory disorder is monitored, simultaneously with assisting the rat's walking motion, based on the biosignals detected from the intended in vivo site (spinal cord, cranial nerve or the like) while causing the rat to engage in a walking motion.

In the foregoing case, foremost, a catheter is indwelled in vivo in a state of being inserted from the rat's urethral opening up to the bladder via the urethra. Next, urine is collected by injecting water into the bladder via the catheter, or through self-production of urine. Subsequently, the urination phenomenon from the urine collection period to the urination period is reproduced by causing the rat to discharge the liquid accumulated in the bladder.

Here, the urinary function is evaluated by monitoring in detail the activity of the bladder and/or the urethra, and the diagnosis of the urination disorder and the analysis of the disease state are performed based on the evaluation result. As specific examples of this kind of urinary function study, considered may be urinary flow measurement, residual urine measurement, bladder internal pressure measurement, urethra internal pressure measurement, pressure flow study, external sphincter electromyogram, and bladder/urethra contrast radiography.

As the actual monitoring method, a monitoring/measurement unit (not shown) according to the method of the urinary function study is provided within the control device 17 (FIG. 3). Moreover, the evaluation of the urinary function may also be performed in the foregoing external device 25 (FIG. 3) by the control device 17 of the functional improvement evaluation apparatus 1 sending the measurement data of the monitoring/measurement unit to the external device 25 (FIG. 3) via the transmission/reception unit 13.

Even in the foregoing embodiment, it is also possible to provide an electrostimulation sensor in substitute for, or integrally with, the biosignal detection sensor as described above, determine the electrostimulation to be applied to the bladder based on the biosignals, and thereby apply electrostimulation from the electrostimulation sensor.

(5-3) Neural Transmission Functional Improvement Evaluation Method (Nerve Cell Culture Method)

Example of this Embodiment

The culture condition of nerve cells of this embodiment is foremost explained as the premise. In this embodiment, the appropriate culture condition of nerve cells may be suitably selected by those skilled in the art among the publicly known culture conditions for the nerve cells to be used. The culture method of nerve cells in this embodiment is not limited to the nerve cell culturing of the rat to be evaluated, and may also be applied broadly to the nerve cell culturing of other rats and various other mammals (including humans).

There is no particular limitation regarding the culture medium to be used, and publicly known culture mediums may be used for culturing the nerve cells. Moreover, the culture medium may also contain fetal bovine serum (FBS), neonatal calf serum, equine serum or other serum.

As the incubator to be used in culturing the cells, a $CO_2$ incubator similar to a type that is used for general cell culturing of nerve cells may be used for maintaining the carbon dioxide (CO2) concentration in the culture medium at a predetermined value. Generally speaking, nerve cells are cultured under the culture condition where the CO2 concentration is 5% to 10%, temperature is 28° C. to 37° C., and relative humidity is roughly 80%. Moreover, an O2 incubator may also be used for maintaining the oxygen (O2) concentration in the culture medium at a predetermined value.

Moreover, upon culturing nerve cells, it is preferable to add, to the culture medium, the neuro growth factor (hereinafter sometimes referred to as "NGF") which is secreted from the nerve cells. Nerve cells are seeded on a nerve cell culturing substrate, and cultured by being left in a CO2 incubator for a predetermined period. After the colonization of the nerve cells, the culture medium may be exchanged for each predetermined period. The subsequent culture medium may be a serum culture medium, a serum-free culture medium, or a culture medium added with cytokine or the like. There is no particular limitation regarding the culture substrate, and, for example, a plastic culture dish such as a Petri dish, or a conventional culture substrate such as a watch glass may be used.

Figure 8:
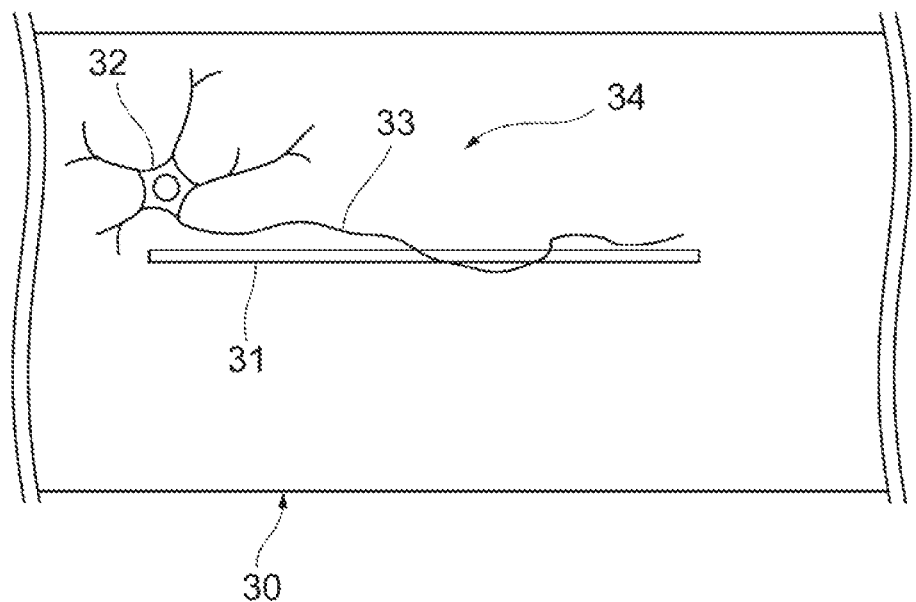
FIG. 8 is a schematic diagram explaining the culture method of nerve cells according to this embodiment.

FIG. 8 is a schematic diagram explaining the culture method of nerve cells according to this embodiment. A nanofiber 31 and a nerve cell 32 are disposed on a culture substrate 30. Here, the nerve cell 32 is disposed near the entrance or within the nanofiber 31. By culturing the nerve cell 32 in this state, the neurite of the nerve cell 32 will grow along the elongation direction (axis direction) of the nanofiber 31.

In other words, by controlling the elongation direction of the nanofiber 31, the nerve cell 32 can be elongated in the intended direction. Here, the nanofiber 31 plays the role as a guide member which guides the growth of the neurite 33.

While the number of nanofibers 31 in FIG. 8 is one nanofiber, the present invention is not limited thereto, and two or more nanofibers 31 may also be disposed. Moreover, there is no particular limitation regarding the diameter of the nanofiber 31, and standard commercially available nanofibers may be used.

As the material of the nanofiber 31, there is no particular limitation so as long as the material has biocompatibility, and nanofibers made from an inorganic material, an organic material and/or an inorganic/organic composite material may be used. As an inorganic material, for example, a carbon nanofiber material may be used. Moreover, as an organic material, for example, a cellulosic or synthetic polymer nanofiber may be used.

With the foregoing culture method of nerve cells, it has been confirmed that the nerve cell 32 grows along the elongation direction of the nanofiber 31 at an order of approximately 3 mm/day under the foregoing culture condition.

The nanofiber 31 and the nerve cell 32 can be applied to the damaged area of the nerve cells and be used as an implant module 34 for restoring the damaged area.

Figure 9:
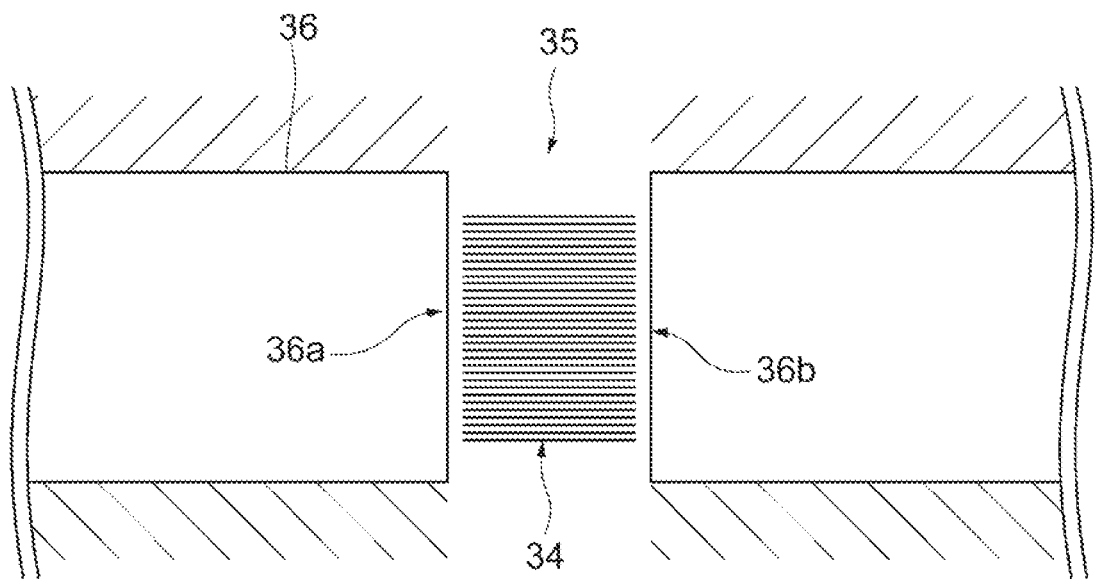
FIG. 9 is a schematic diagram explaining a method of applying the nerve cells, which were cultured according to the culture method of this embodiment, to the damaged area of the nerve cells.

FIG. 9 is a schematic diagram explaining a method of applying the nerve cells, which were cultured according to the culture method of this embodiment, to the damaged area of the nerve cells.

While this embodiment will explain a case of applying the implant module 34 to a spinal cord 36 having a damaged area 35, the present invention is not limited to this point. The damaged area 35 is any area or location in which the nerve cell 32 is damaged or ruptured. The implant module 34, which preferably contains a plurality of arranged nanofibers 31 and cultured nerve cells 32, is implanted in the damaged area 35.

The nerve cells 32 are preferably cultured to be a predetermined length based on the foregoing culture method according to the damage length of the damaged area 35. The nanofibers 31 are formed from a material having biocompatibility. Thus, the implant module 34 containing the nanofibers 31 and the nerve cells 32 can be directly implanted in the damaged area 35.

Here, a supporting member (not shown) for supporting the implant module 34 at the damaged area 35 may also be disposed. There is no particular limitation regarding the supporting member so as long as it has biocompatibility and is able to retain the nanofibers 31 and the nerve cells 32 at the damaged area 35.

The nerve cells 32 implanted by the nanofibers 31 are in a state of easily growing in a predetermined direction, or growing in a predetermined direction. As a result of implanting the implant module 34, it is possible to increase the possibility of the nerve cells (not shown) positioned at two opposing end faces 36a, 36b via the damaged area 35 in the spinal cord 36 becoming connected with the implanted nerve cells 32. In other words, it is possible to easily restore the restoration of the damaged area 35.

The implant module 34 preferably includes one or more electrodes. Preferably, a plurality of electrodes are disposed radially around the location where the electrodes are to be implanted (i.e., damaged area 35). Consequently, the cell activity of the nerve cells can be examined by measuring the changes in the nerve action potential. Furthermore, in the foregoing case, a subcutaneous implanted electrode is preferably disposed on the muscle surface corresponding to the damaged area 35. By comparing the biopotential of the electrodes disposed in the damaged area 35 and the biopotential of the subcutaneous implanted electrode disposed on the muscle surface corresponding to the damaged area 35, it is possible to estimate the transmission concreteness of the neural transmission signals; that is, the restoration level of the damaged area. Moreover, electrostimulation by way of a square wave current or the like may also be input into the electrodes.

Moreover, electrostimulation by way of a square wave current or the like may also be input into the electrodes. Moreover, by measuring the action potential that was reflected in response to external electrostimulation, it is possible to monitor the cell activity of the nerve cells in further detail. Furthermore, it is possible to control the directivity of the elongation of the nerve cells by controlling the stimulation frequency of the electrostimulation based on the relationship of the monitored action potential and cell activity.

For example, there is no particular limitation regarding the current intensity, pulse duration and waveform tilt in cases of inputting electrostimulation by way of a square wave current so as long as it is possible to stimulate the nerve fibers. Moreover, the electrification method may be based on unipolar electrification or bipolar electrification.

After implanting the implant module 34, a culture medium containing NGF, O2 or CO2 is preferably supplied to the implant module 34 via a flow channel such as a pipe by using a pump or the like. Consequently, the implant module 34 is cultured under conditions that are similar to an environment where cells are viable in an organism similar to the culture condition described above. Thus, because the growth of the nerve cells 32 is further promoted, the damaged area 35 can be restored at an even higher probability.

The implant module 34 and the implant modules 40 to 42 described later (FIG. 13 to FIG. 15) can be stocked via cryopreservation. In the foregoing case, the implant module may be defrosted and used as needed.

In the culture method of nerve cells according to this embodiment described above, a nanofiber 31 is used as a guide member for guiding the nerve cells. Because the nerve cells 32 grow along the elongation direction of the nanofiber 31, the nerve cells 32 can be grown in the intended direction by disposing the nanofiber 31 in the intended elongation direction.

An example which demonstrated that the nerve cells can actually be elongated in a predetermined direction using a guide member is now explained.

In this embodiment, PC-12 cells were used as the model cells. It is known that, with the PC-12 cells, which are a cell line established from rat adrenal medulla chromaffinity cytoma, the neurites become elongated based on the effect of NGF, and become branched into nerve cell-like cells.

The PC-12 cells were bonded to BD PuraMatrix peptide hydrogel (manufactured by 3-D Matrix, Ltd.), and the cell process was elongated in all culture conditions. The cell density was set to 8×104 cells/ml, and the cells were cultured for 8 days under all culture conditions after adding NGF.

Figure 10:
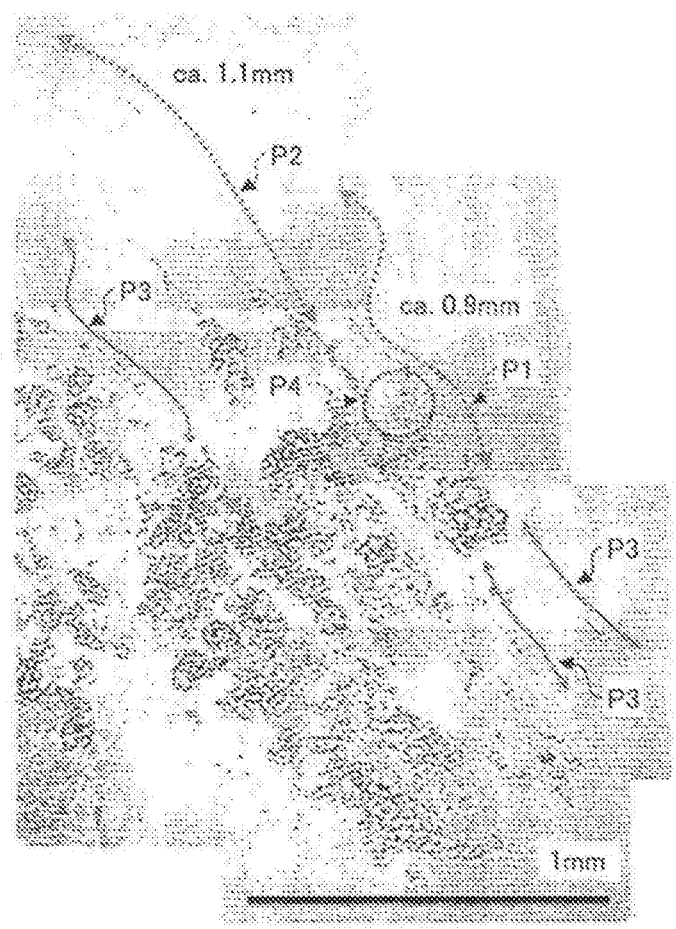
FIG. 10 is a diagram showing an example of a phase-contrast micrograph of the nerve cells according to this embodiment.

FIG. 10 is a diagram showing an example of a phase-contrast micrograph of the nerve cells according to this embodiment. As shown in FIG. 10, with the PC-12 cells, it can be understood that the neurites become elongated primarily based on the following four patterns:

Pattern 1 (P1): Pattern of becoming elongated toward the edge of the gel or along the edge of the gel;

Pattern 2 (P2): Pattern of becoming elongated in parallel with the unevenness of the gel;

Pattern 3 (P3): Pattern of becoming elongated toward other cells; and

Pattern 4 (P4): Pattern of becoming elongated radially.

Figure 11:
FIGS. 11(a)-11(b) is a diagram showing another example of a phase-contrast micrograph and a fluorescence micrograph of the nerve cells according to this embodiment.
Figure 11:
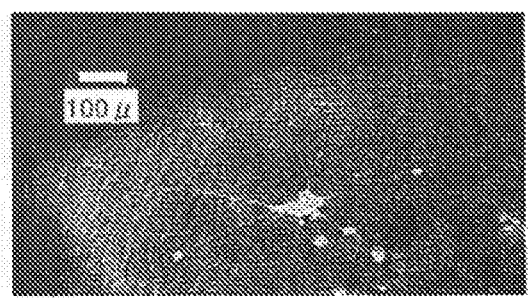

In order to explain the foregoing four patterns in further detail, FIG. 11(*a*) shows a phase-contrast micrograph of the nerve cells according to this embodiment, and FIG. 11(*b*) shows another example of the fluorescence micrograph. Moreover, FIG. 12(*a*) shows a phase-contrast micrograph of the nerve cells according to this embodiment, and FIG. 12(*b*) shows another example of the fluorescence micrograph.

From the photographs of FIG. 11(*a*) and FIG. 11(*b*), it has been observed that the PC-12 cells are elongated radially and toward other cells. Moreover, from the photographs of FIG. 12(*a*) and FIG. 12(*b*), it has been observed that the PC-12 cells are elongated toward the edge of the gel or along the edge of the gel, and in parallel with the unevenness of the gel.

Based on the foregoing results, it can be understood that the elongation direction of the PC-12 cells is affected by the footing where the cells are disposed, the unevenness of the gel, and the aggregation of the cells. In other words, by using a guide member having predetermined regular or irregular directionality, it is possible to control the elongation direction of the nerve cells in a predetermined direction.

With the culture method of nerve cells according to this embodiment described above, it is possible to cause the nerve cells to become elongated with an intended directionality. Moreover, because an implant module containing the nerve cells and the guide member is able to cause the nerve cells to become elongated with an intended directionality, the implant module can be generically applied to damaged areas.

First Modified Example

As a first modified example of this embodiment, the same effects as those described above can be yielded even upon applying a hollow nanofiber 50 shown in FIG. 13, in which an internal space is formed along the longitudinal direction, in substitute for the general nanofiber 31 (FIG. 8). In the foregoing case, one nerve cell 32 or two or more nerve cells 32 may be disposed in one hollow nanofiber 50. Moreover, while there is no particular limitation regarding the diameter of the hollow nanofiber 50 so as long as it is possible to the dispose the nerve cells 32 therein, the diameter is preferably 10 µm to 100 µm.

Second Modified Example

Figure 14:
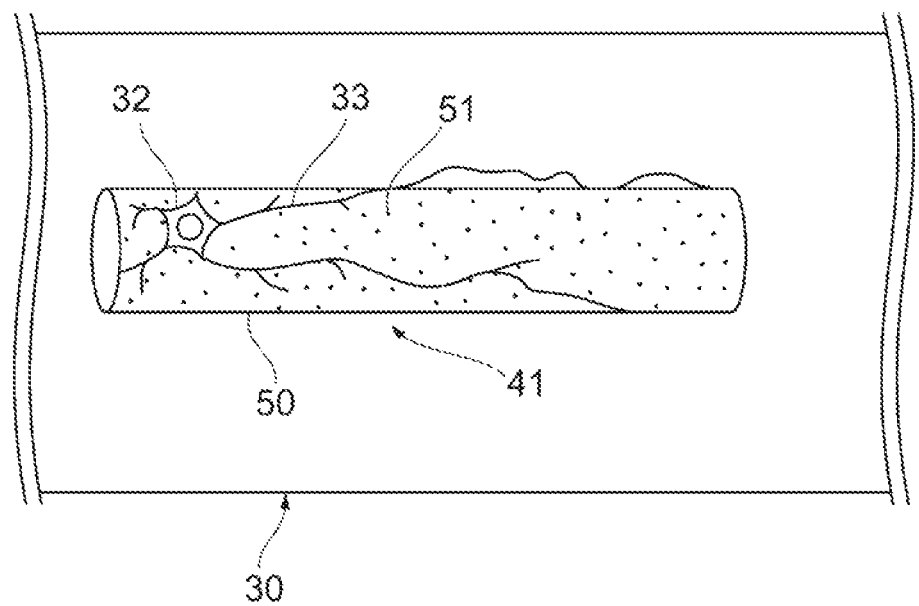
FIG. 14 is a conceptual diagram explaining a second modified example of the culture method of nerve cells according to this embodiment.

Moreover, as a second modified example of this embodiment, as shown in FIG. 14, a hollow nanofiber 50 having minute holes in communication from the outer surface to the inner surface, and the nerve cells 23, may be disposed on the culture substrate 30. Because the hollow nanofiber 50 has a plurality of minute holes 51, the neurites 33 that reach the inner surface of the hollow nanofiber 50 during growth go out to the outer surface of the hollow nanofiber 50 through the respective holes 51. The neurites 33 on the outer surface additionally grow along the outer surface; that is, along the elongation direction of the hollow nanofiber 50. There is no particular limitation regarding the diameter of the holes 51 so as long as the neurites 33 can pass therethrough.

Third Modified Example

Figure 15:
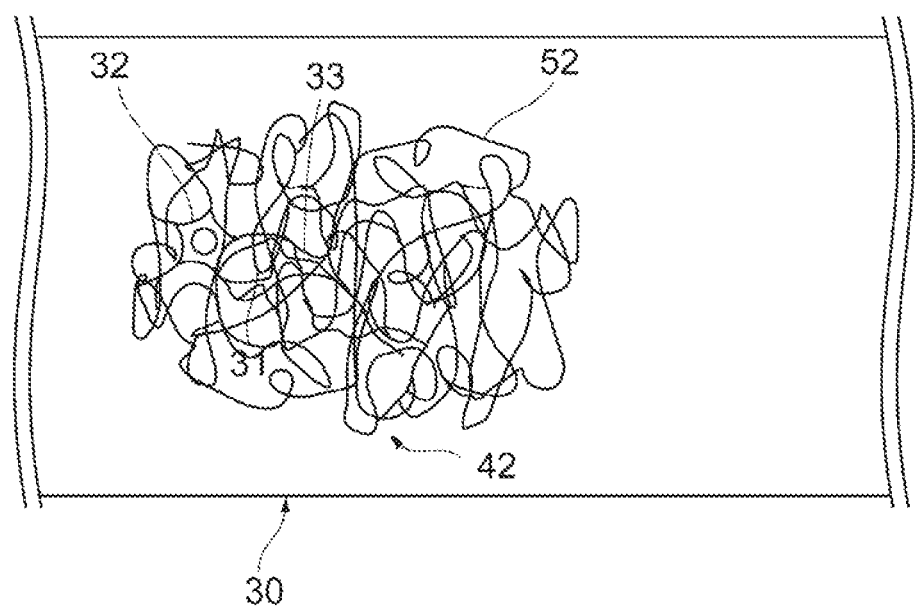
FIG. 15 is a conceptual diagram explaining a third modified example of the culture method of nerve cells according to this embodiment.

Furthermore, as a third modified example of this embodiment, as shown in FIG. 15, a nanofiber 52 formed in a cloud shape and a nerve cell 32 may be disposed on the culture substrate 30. Here, a nanofiber 52 formed in a cloud shape refers to a nanofiber or a nanofiber group which is formed by one or more nanofibers becoming elongated regularly or irregularly.

By using the nanofiber 52 formed in a cloud shape, it is possible to cause the neurite 33 of the nerve cell 32 to grow in correspondence with the elongation direction of a nanofiber which becomes elongated regularly or irregularly. In other words, the nanofiber 52 formed in a cloud shape plays a role as a guide member which enables the neurite 33 to grow with a predetermined directionality having a greater degree of freedom in comparison to a case of growing in a single direction. As the material of the nanofiber 52, an inorganic material or an organic material with biocompatibility may be used as with the hollow nanofiber 50 described above.

The nanofiber 52 and the nerve cell 32 formed in a cloud shape may also be applied to the damaged area of the nerve cells and used as an implant module 42 for restoring the damaged area in the same manner as the first and second modified examples described above.

Figure 16:
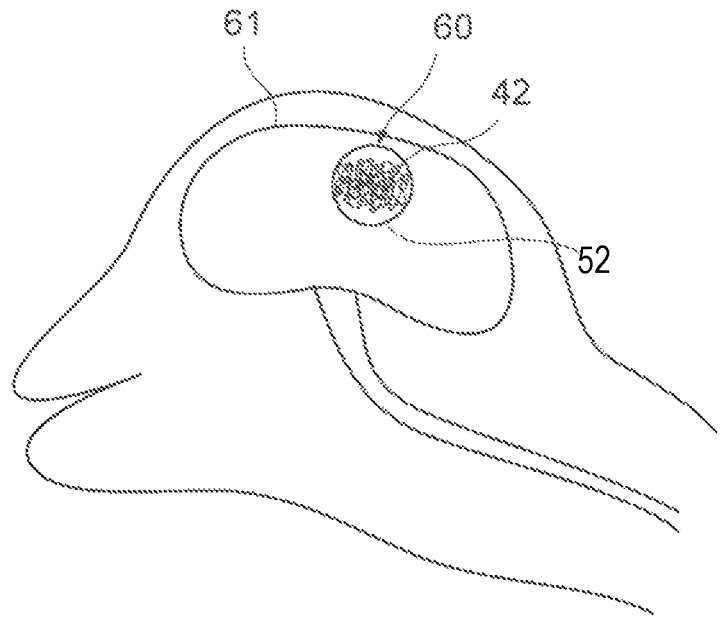
FIGS. 16(a)-16(b) is a schematic diagram explaining a second modified example of a method of applying the nerve cells, which were cultured according to the culture method of this embodiment, to the damaged area of the nerve cells.
Figure 16:
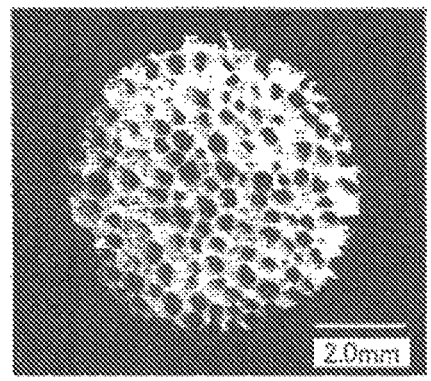

FIG. 16(*a*) is a schematic diagram explaining another example of a method of applying the nerve cells 32, which were cultured according to the culture method of the third modified example, to the damaged area of the nerve cells. Moreover, FIG. 16(*b*) is an optical micrograph of an example of the implant module 42 including the nanofiber 52 formed in a cloud shape according to the third modified example.

In a case of applying the cultured nerve cell 32 to a cranial nerve 61 having a damaged area 60, the damaged area 60 refers to the area or location of a hole within the cranial nerve formed due to cerebral infarction or the like as shown in FIG. 16. An implant module 42 containing the nanofiber 52 formed in a cloud shape and the cultured nerve cell 32 is implanted in the damaged area 60. The size and shape of the nanofiber 52 are set in advance to match the size and shape of the damaged area 60.

As this kind of implant module 42, desirably used is a type in which the neurite 33 of the nerve cell 32 has grown, for instance, up to the substantial surface of the implant module 42. When implanting the implant module 42 in the damaged area 60, a supporting member (not shown) for supporting the implant module 42 at the damaged area 60 may also be disposed.

The nerve cell 32 in the implant module 42 has grown up to the substantial surface of the implant module 42. As a result of implanting the implant module 42, it is possible to increase the possibility of the nerve cell 32 becoming connected with the nerve cells positioned at a marginal part facing the damaged area 60 in the brain cells. In other words, it is possible to easily restore the restoration of the damaged area 60.

After implanting the implant module 42, a culture medium containing NGF, $O_2$ or $CO_2$ is preferably supplied to the implant module 42 via a flow channel such as a pipe (not shown). Consequently, the implant module 42 is cultured under conditions that are similar to an environment where cells are viable in an organism similar to the culture condition described above. Thus, because the growth of the nerve cells 32 is further promoted, the damaged area 60 can be restored at an even higher probability.

The implant module 42 preferably includes one or more electrodes as with the foregoing implant modules 40, 41. Preferably, a plurality of electrodes are disposed radially around the location where the electrodes are to be implanted (i.e., damaged area 60). Consequently, the cell activity of the nerve cells 32 can be examined by measuring the changes in the nerve action potential. Furthermore, in the foregoing case, a subcutaneous implanted electrode is preferably disposed on the muscle surface corresponding to the damaged area 60. By comparing the biopotential of the electrodes disposed in the damaged area 60 and the biopotential of the subcutaneous implanted electrode disposed on the muscle surface corresponding to the damaged area 60, it is possible to estimate the transmission concreteness of the neural transmission signals; that is, the restoration level of the damaged area 60. Moreover, electrostimulation by way of a square wave current or the like may also be input into the electrodes.

In the culture method of nerve cells according to this embodiment described above, a nanofiber 52 formed in a cloud shape is used as the guide member of the nerve cells 32. Because the nerve cells 32 grow in correspondence with the elongation direction of the nanofiber 52, the nerve cells 32 can be grown with a high degree of freedom while possessing a predetermined directionality.

(6) Functional Improvement Evaluation Apparatus According to Other Embodiments (6-1) Expanded Application to Primates as Model Animals While the foregoing embodiment explained a case of applying the present invention to quadrupedal walking mammals such as rats as the model animal, the present invention is not limited thereto, and the present invention may also be broadly applied to non-human primates such as monkeys.

For example, while monkeys are primates as with humans, because monkeys engage in quadrupedal walking referred to as "knuckle walking" in which their front limbs come into contact with the ground in the state of a clenched fist, their manner of walking is considerably different from humans that engage in erect bipedalism. The head of a monkey is not positioned on the centroidal line on the body as with humans, and the angle that connects the cervical spine and the skull is also considerably different in comparison to humans. Moreover, while the spine of monkeys is straight, the spine of humans forms an S-shape, and becomes thicker and stronger as the lower it becomes.

Accordingly, while monkeys are common with humans in that they are primate mammals, because their body size and functions pertaining to the mechanical load of the spine are different, it is difficult to apply a support system for humans based on bioelectric potential signal simply by improving the support system, and it is desirable to modify the support system so that it can be applied to monkeys as a model animal.

When applying a monkey as a model animal, in addition to implanting a sensor in vivo as with small mammals such as a rat, a sensory may also be provided noninvasively on the monkey's skin surface.

The sensor (biosignal detection unit) to be mounted on the monkey's skin surface is mounted, as with small mammals such as a rat, on a central side above an intended in vivo site (for example, spinal cord injury site or nerve ruptured area) and/or a peripheral side which is below the intended in vivo site, and detects biosignals (bioelectric potential signals such as muscle potential signals and neural transmission signals) resulting from a biological activity of the monkey.

The sensor is mounted so that it is attached to the skin surface around the monkey's joint (around the muscles that are used upon moving the joint) by using an adhesive seal that covers the periphery of the sensor.

Similar to humans, acetylcholine as a synapse transmission substance is discharged in monkeys to the surface of the muscles forming the skeletal muscle based on commands from the brain, and, as a result, the ionic permeability of the sarcolemmal membrane changes and action potential is generated. And based on the action potential, the muscle fibers become contracted, and muscular strength is thereby generated. Thus, it is possible to estimate the muscular strength that is generated during the movement by detecting the potential of the skeletal muscles, and obtain the assist force that is required for the movement from the virtual torque based on the estimated muscular strength.

By assisting the monkey's walking motion as described above, it is possible to artificially build a nerve system loop and promote the in vivo/in vitro interactive bio feedback between the brain/nerve system (central nervous system) and the musculoskeletal system (peripheral system/body), and thereby establish a technology for promoting functional improvement.

In the case of this embodiment also, without limitation to the detection of the nerve action potential by a sensor (biosignal detection unit), it is also possible to apply electrostimulation to biotissues from a sensor. In other words, the walking motion assist device may additionally comprise a sensor for detecting the nerve action potential, and a sensor for applying electrostimulation to biotissues. For example, the potential detection sensor detects the nerve action potential in a path (for example, the spinal cord ascending tract) which ascends toward the upper nerve center (for example, the brain). The electrostimulation sensor (biostimulation application unit) applies electrostimulation in a path (for example, the spinal cord descending tract) which descends from the upper nerve center. Consequently, even in cases where the spinal cord is ruptured, it is possible to move parts or acquire sensations on a side that is lower than the ruptured area. It is also possible to determine the electrostimulation to be applied to the biotissues based on the nerve action potential detected in the ascending tract, and thereby apply electrostimulation from the stimulation sensor.

Furthermore, in addition to affixing a plurality of sensors (biosignal detection units) on the monkey's skin surface, a plug suit comprising a sensor group arranged in even intervals along the flow of the monkey's leg muscles (for example, refer to Japanese Patent Application Publication No. 2013-179966) may also be mounted on the monkey.

While the foregoing embodiment explained a case of applying an electrostimulation sensor as the biostimulation application unit that is provided in substitute for, or integrally with, the sensor (biosignal detection unit), the present invention is not limited thereto, and, so as long as physical stimulation can be applied to the model animal, in addition to electrical stimulation, various other physical stimulation application means capable of applying vibration-based mechanical stimulation, thermal stimulation based on temperature change, magnetic stimulation or ultrasonic stimulation may also be broadly applied.

Figure 17:
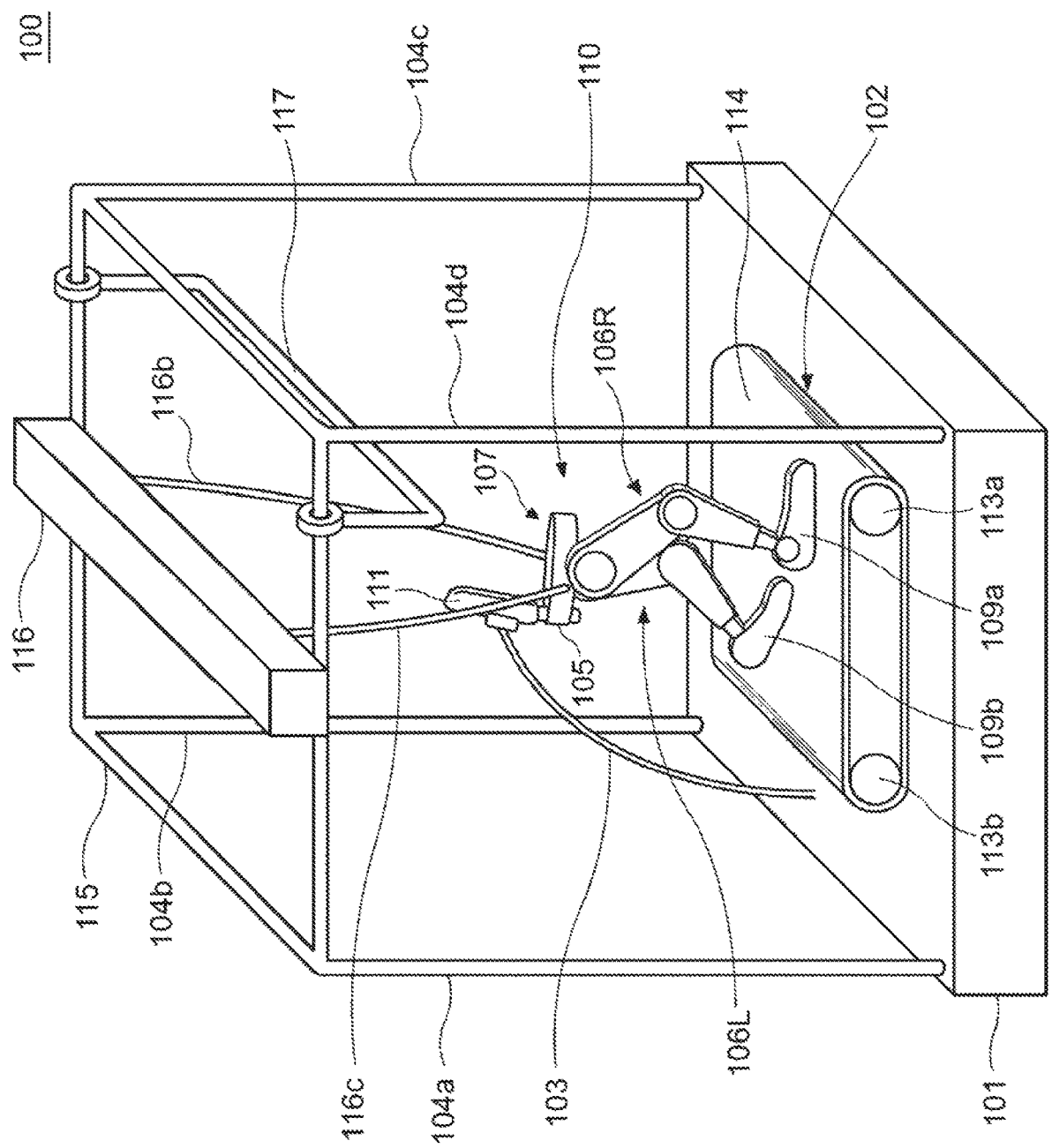
FIG. 17 is an external perspective view of a functional improvement evaluation apparatus for evaluating the functional improvement of a rat according to another embodiment of the present invention.

(6-2) Overall Configuration of Functional Improvement Apparatus According to Other Embodiments FIG. 17 is an external perspective view of the functional improvement evaluation apparatus 100 for evaluating the functional improvement of a monkey according to another embodiment. With the functional improvement evaluation apparatus 100, treadmill 102 is disposed on a base 101, and a control unit 120 (FIG. 19) is built in below the treadmill 102.

The control unit 120 is conductively connected to a body-worn motion assist device 110, which is used for assisting the monkey's walking motion, via a communication cable 103. The control unit 120 includes a control device 131 (FIG. 19) and a power supply circuit described later, and is configured to send and receive signals and supply power to and from the body-worn motion assist device 110, and detect the bioelectric potential signals from a sensor 122 (FIG. 19) mounted on the monkey.

The body-worn motion assist device 110 generates power according to the monkey's intent based on the biosignals (for example, signals such as the surface myoelectric potential output from the monkey's body) resulting from the monkey's walking motion, classifies the respective movement patterns of the monkey into tasks configured from a series of phases (minimal movement units), estimates the phase of the monkey's task by using physical quantities of the rotation angle of the monkey's leg joints and the floor reaction, and thereby generates power according to the estimated phase.

With the body-worn motion assist device 110, a plurality of frames 104a to 104d formed along the monkey's lumbar region and skeleton of the lower limb are rotatably connected at positions corresponding to the respective joints of the monkey, and a driving source 123 (FIG. 19) is provided to a position corresponding to a predetermined joint (position corresponding to a joint which requires assistance).

In other words, the body-worn motion assist device 110 includes a motion transmission mechanism 107 configured from a waist frame 105 to be mounted on the monkey's waist, a right leg assist part 106R provided downward from the right side of the waist frame 105, and a left leg assist part 106L provided downward from the left side of the waist frame 105.

Figure 18:
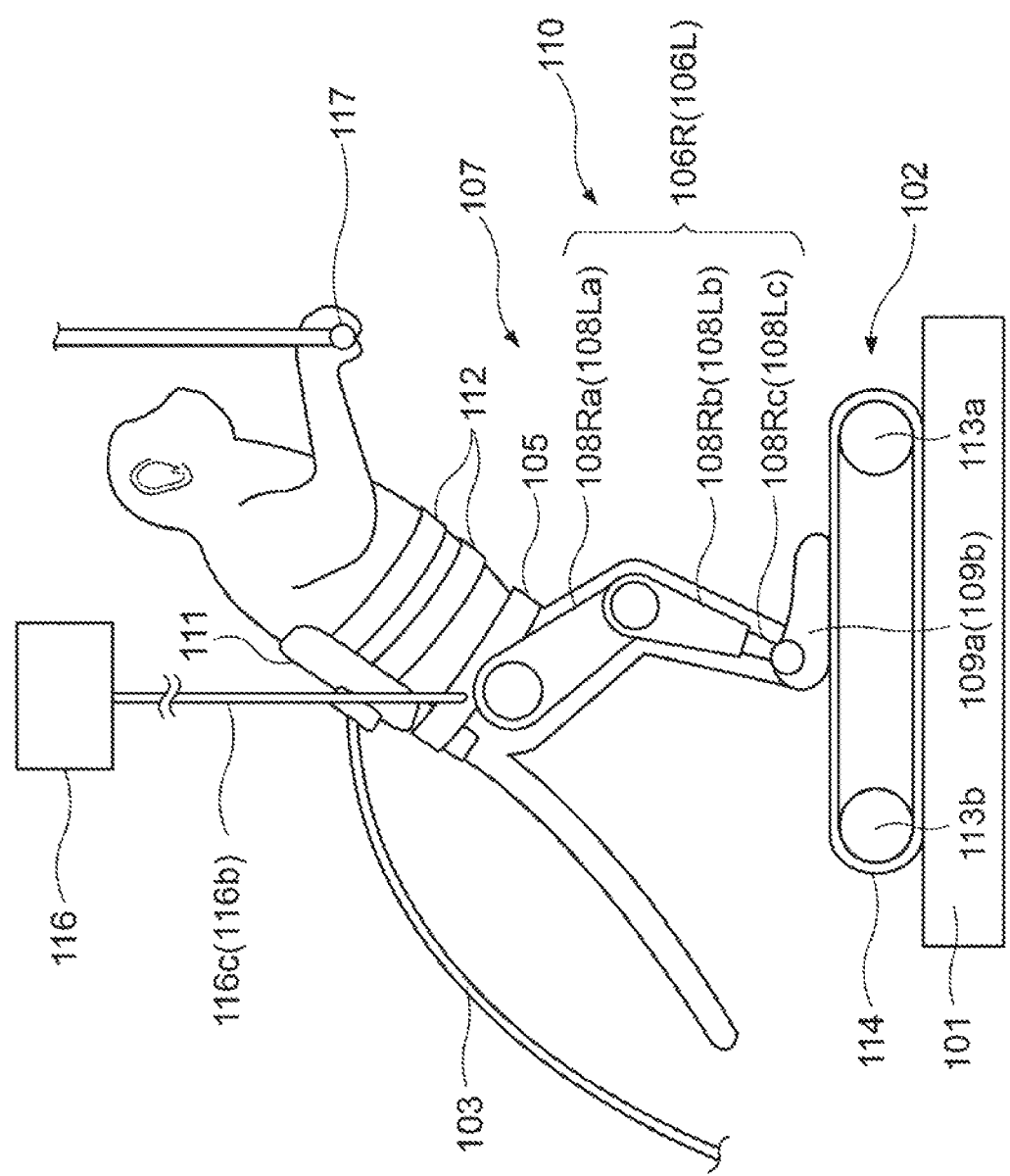
FIG. 18 is a conceptual diagram explaining a state where a rat has been set in the functional improvement evaluation apparatus according to this embodiment.

As shown in FIG. 18, the right leg assist part 106R and the left leg assist part 106L are provided to be mutually symmetrical, extend downward from the waist frame 105, and include first frames 108Ra, 108La formed along the outer surface of the monkey's thighs, second frames 108Rb, 108Lb extending downward from the first frames 108Ra, 108La and formed along the outer surface of the monkey's shin, and third frames 108Rc, 108Lc mounted on the shoes to be worn by the monkey's feet.

Among the above, an actuator (drive motor) corresponding to the driving source 123 is provided at the connecting region of the waist frame 105 and the first frames 108Ra, 108La and at the connecting region of the first frames 108Ra, 108La and the second frames 108Rb, 108Lb, respectively. These drive motors are driving sources configured from a servo motor in which the drive torque is controlled based on the control signals from the control unit 120, and include a reduction mechanism for reducing the motor rotation at a predetermined reduction ratio, and are able to supply sufficient power despite their small size.

Furthermore, each drive motor (123) includes an angle sensor (not shown) which detects the rotation angle (i.e., joint angle) of the connecting regions of the frames 105, 108R, 108L. The angle sensor is configured, for example, from a rotary encoder which counts the number of pulses proportional to the joint angle, and outputs, as a sensor output, electric signals corresponding to the number of pulses according to the joint angle. Each angle sensor detects the rotation angle between the waist frame 105 and the first frames 108Ra, 108La which corresponds to the joint angle of the monkey's hip joint, and the rotation angle between the lower end of the first frames 108Ra, 108La and the second frames 108Rb, 108Lb which corresponds to the joint angle of the monkey's knee joint.

The connecting regions of the frames 105, 108R, 108L are configured so that they will rotate only within the angular range in which the monkey's hip joint and knee joint can rotate, and a stopper mechanism (not shown) for preventing the unreasonable movement of the monkey's hip joint and knee joint is built therein.

Furthermore, the pair of special-purpose shoes 109a, 109b is provided with a centroid sensor (not shown) such as a strain sensor (strain gauge) on the sole to measure the load on the underside of the monkey's feet, and detect the movement of the centroid position based on changes in the measured load.

Moreover, the body-worn motion assist device 110 includes a drive back 111 to be mounted on the monkey's back, and houses, for instance, a motor driver and a display device. Moreover, the drive back 111 is the part that is connected when the control unit 120 (FIG. 19) is to be connected externally via the communication cable 103. Note that the drive back 111 is supported by the waist frame 105 of the motion transmission mechanism 107 and, even when the monkey's body is retained with the waist belt 112, the weight of the drive back 111 will not be a burden on the monkey.

When the body-worn motion assist device 110 sends the biosignals from the joint angle detection unit 132 (FIG. 19) to the control unit 120 via the drive back 111 as described above, the control unit 120 controls the operation of the respective motor drivers, power supply circuit and other equipment in the overall functional improvement evaluation apparatus 100, including the body-worn motion assist device 110, based on the acquired biosignals.

The treadmill 102 (FIG. 17) includes a walking belt 114 which moves in a circular motion according to the rotation of rollers 113a, 113b. The walking belt 114 is arranged horizontally. A motor 102a (FIG. 19) can rotate the rollers 113a, 113b via a transmission mechanism. The circulation speed of the walking belt can be changed by changing the rotation speed of the rollers 113a, 113b. Furthermore, the walking belt 114 can be inclined in the front-back direction like a slope, and the load of the walking motion can be increased by causing the slope to become steep, and the load of the walking motion can be reduced by causing the slope to be more horizontal.

Furthermore, support columns 104a to 104d are erected at each of the four corners on the upper face of the base 101, and a support frame 115 is connected to the upper end of the support columns 104a to 104d so that the overall apparatus configures a substantial rectangular parallelepiped frame body. A relief device 116 is placed across the support frame 115, and is able to freely slide and move along the juxtaposed direction of the treadmill 102 and the walking belt 114.

Moreover, a holding part 117 to be held by the monkey's hands is placed across the support frame 115, and is able to freely slide along a direction that is parallel to the walking belt 114 of the treadmill 102, and the height thereof can also be freely adjusted in a vertical direction.

The relief device 116 includes a servo motor 116a (FIG. 19) which is conductively connected with the body-worn motion assist device 110, and, for instance, is connected to one end of suspending harnesses 116b, 116c. The left and right regions of the waist frame 105 of the motion transmission mechanism 107 are connected to the other end of the harnesses 116b, 116c.

The relief of the load on the monkey's feet is determined depending on the extent that the servo motor 116a (FIG. 19) lifts the harnesses 116b, 116c. The higher the harnesses 116b, 116c are lifted, the relief will increase, and the load on the monkey's feet will decrease.

Moreover, the functional improvement evaluation apparatus 1 is additionally provided with an input unit 118 (FIG. 19) for adjusting the rotation speed of the rollers 113a, 113b based on the motor 102a in the treadmill 102, and the relief provided by the relief device 118. By using the input unit 118, the outside operator can adjust the speed of the walking belt 114 and the load on a pair of pair of special-purpose shoes 109a, 109b. For example, the input unit 118 can be used to set the speed of the walking belt 114 to be roughly the same as the walking speed of monkeys.

FIG. 18 shows a case where a monkey is set in the functional improvement evaluation apparatus 100 configured as described above. Foremost, the body-worn motion assist device 110 is mounted on the monkey's lower limbs, and special-purpose shoes 109a, 109b are each placed on a pair of forefeet of the monkey. Next, while retaining the monkey's body with the waist belt 112, the left and right regions of the waist frame 105 corresponding to the monkey's waist are respectively connected to the harnesses 116b, 116c, and thereby connected to the relief device 116.

The monkey is caused to hold the holding part 117 while the pair of special-purpose shoes 109a, 109b adjusts the load on the walking belt 114 of the treadmill 102 based on the relief device 116.

In this state, when a video monitor or an item of interest (interesting object or favorite food or the like) is placed in front of the monkey and the walking belt 114 of the treadmill 102 is moved at an optimal speed, the monkey will independently start its walking motion, and take one step at a time on the walking belt 114 of the treadmill 102 with the special-purpose shoes 109a, 109b b worn on the feet of the pair of back legs.

Furthermore, the functional improvement evaluation apparatus 100 detects the bioelectric potential signals that are generated when the monkey moves its muscles, controls the drive torque from the driving source 123 (FIG. 19) based on the detected bioelectric potential signals, and thereby transmits the drive torque to the pair of special-purpose shoes 109a, 109b and applies assist force (power) to each of the monkey's legs.

(6-3) Configuration of Control System of Functional Improvement Apparatus

Figure 19:
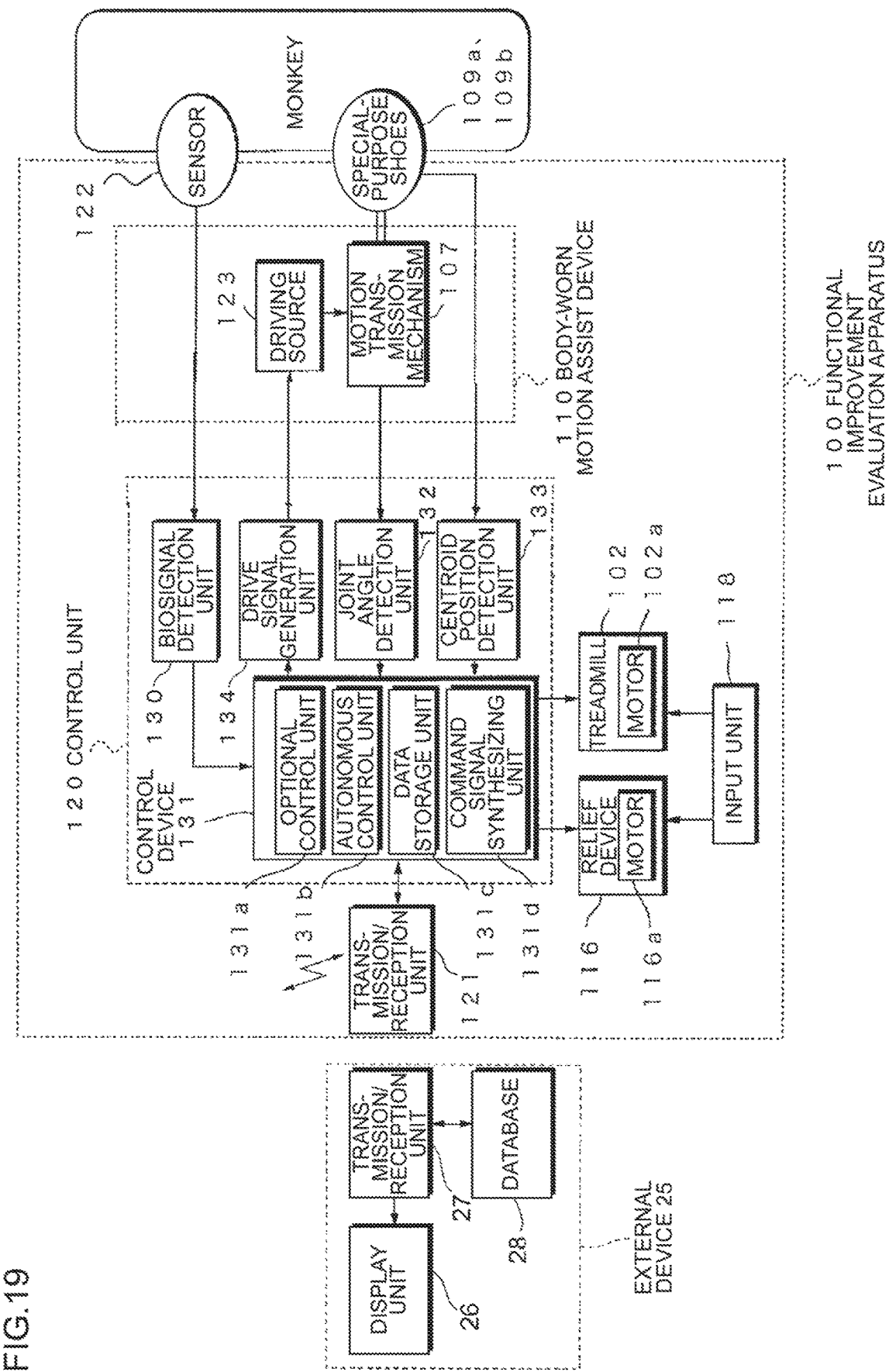
FIG. 19 is a block diagram showing a configuration of the control system of the functional improvement evaluation apparatus according to this embodiment.

FIG. 19 is a block diagram showing a configuration of the control system of the functional improvement evaluation apparatus 100 according to another embodiment. The functional improvement evaluation apparatus 100 comprises a body-worn motion assist device 110, a relief device 116, a treadmill 102, and a transmission/reception unit 121.

In the control unit 120, a biosignal detection unit 130 detects bioelectric potential signals from a sensor, which is mounted on the skin surface of a monkey wearing the body-worn motion assist device 110, when the monkey moves its muscles around its joints. For example, in cases where the monkey's spinal cord is ruptured or damaged and the nerves do not sufficiently reach its legs, the sensor is implanted above the ruptured area or the damaged area (on the side that is closer to the brain), and the nerve action potential is detected from the nerve fibers.

The biosignal detection unit 130 sends the bioelectric potential signals detected by the sensor 122 to a control device 131. A joint angle detection unit 132 detects the rotation angle of a connecting region between the respective frames according to the monkey's movement as the joint angle of the femoral joint and the knee joint of the monkey's legs, and outputs the detected rotation angle to the control device 131. An angle sensor (not shown) is used as the joint angle detection unit 132.

A centroid position detection unit 133 detects a centroid position according to the monkey's movement from a centroid sensor (not shown) mounted on a pair of special-purpose shoes 109a, 109b, and outputs the detected centroid position to the control device 131. The control device 131 includes an optional control unit 131a, an autonomous control unit 131b, a data storage unit 131c and a command signal synthesizing unit 131d. The optional control unit 131a uses the bioelectric potential signals detected by the biosignal detection unit 130, and generates optional command signals for causing a driving source 123, which is configured from a servo motor in the body-worn motion assist device 110, to generate power according to the monkey's intent.

The data storage unit 131c stores, in a reference parameter database, a task of the monkey's walking motion, and an assist parameter for assisting the monkey's movement according to the task. Moreover, the data storage unit 131c temporarily stores the bioelectric potential signals detected by the biosignal detection unit 130.

Upon analyzing the general walking motion of a monkey in a state where both of the monkey's front arms are holding a fixed part, it can be understood that the typical movement pattern, such as the angle of the respective joints and the movement of the centroid, is predetermined. Thus, the displacement of typical joint angles and the status of shift in the centroid are empirically obtained in relation to the monkey's walking motion, and stored in the reference parameter database. Furthermore, monkeys have different walking patterns depending on their body size, muscle condition, and walking speed. The proper movement pattern will differ depending on the degree of disorder or the progress of rehabilitation of the target monkey. Thus, the corresponding assist pattern will differ even if it is the same task.

The autonomous control unit 131b compares the parameters representing the monkey's movement such as the joint angles detected by the joint angle detection unit 132 and the centroid position detected by the centroid position detection unit 133, and the reference parameters stored in the data storage unit 131c, identifies the task of the monkey's movement and thereafter selects the optimal assist pattern corresponding to the task, and thereby generates autonomous command signals for causing the driving source 123 to generate power according to the assist pattern.

The command signal synthesizing unit 131d synthesizes the optional command signals generated by the optional control unit 131a and the autonomous command signals generated by the autonomous control unit 131b, and outputs the synthesized command signals to a drive signal generation unit 134. The command signal synthesizing unit 131d includes a waveform for causing the driving source 123 to generate power obtained by synthesizing power based on optional control which changes from the start to end of the movement, and power based on autonomous control.

The drive signal generation unit 134 drives the driving source 123 by generating drive signals (drive current) according to the synthesized command signals and supplying the generated drive signals (drive current) to the driving source 123 in the body-worn motion assist device 110. The driving source 123 applies assist force (power) according to the drive signals, via the motion transmission mechanism 107, to each of the monkey's legs.

The transmission/reception unit 121 is a communication device capable of transmission and reception based on a short-range wireless communication technology such as Bluetooth (Registered Trademark) serial communication. The transmission/reception unit 121 modulates, under the control of the control device 131, the reference parameters stored in the data storage unit 131c, the parameters representing the status of the monkey's movement such as the joint angles detected by the joint angle detection unit 132 and the centroid position detected by the centroid position detection unit 133, and the bioelectric potential signals detected by the biosignal detection unit 130 into a predetermined transmission method, and sends the same to an external device 25 via an antenna.

The external device 25 is, for example, a diagnostic computer, and creates electrocardiograms and electroencephalograms and displays them on a display unit 26, uses a transmission/reception unit 27 to receive the various types of data sent from the functional improvement evaluation apparatus 100, and stores the received data in a database 28. Consequently, the external device 25 is able to constantly monitor the monkey's kinetic state and physiological state, as well as manage data in a time series while accumulating such data in the database 28.

As described above, the functional improvement evaluation apparatus 100 applies assist force to the monkey based on the body-worn motion assist device 110 and assists the monkey's walking motion while stabilizing the monkey's position by suspending the monkey with the relief device 116. The control device 131 in the control unit 120 can control the speed of the walking belt 114 of the treadmill 102 based on the monkey's walking speed, as well as control the relief of the relief device 116 based on the monkey's centroid position or the leaning of the monkey's body. Thus, even in cases where the independent movement of the monkey's legs is difficult, the monkey can safely perform its walking motion without having to worry about falling down or straying outside the walking belt 114.

(6-4) Modified Example

While the foregoing embodiment explained a case where the motion transmission mechanism 107 of the body-worn motion assist device 110 was configured substantially in the same manner as an exoskeleton motion assist device to be applied to humans (for instance, refer to Japanese Patent Application Publication No. 2005-95561), the present invention is not limited thereto, and, without providing a driving source to the connection region of the waist frame 105 and the first frames 108Ra, 108La and to the connecting region of the first frames 108Ra, 108La and the second frames 108Rb, 108Lb, and a right leg assist part 106R and a left leg assist part 106L may be used for the walking motion based on switching drive (i.e., tendon drive) according to the tension or relaxation of a wire (not shown).

With the motion transmission mechanism of this modified example, a pair of left and right winding parts (not shown) is provided to the waist frame 105 in the right leg assist part 106R and the left leg assist part 106L, and a pulley (sliding mechanism) to become the center of rotation is provided to the connection region of the waist frame 105 and the first frames 108Ra, 108La and to the connecting region of the first frames 108Ra, 108La and the second frames 108Rb, 108Lb, respectively.

The winding part includes a drive motor configured from a servo motor in which the drive torque is controlled based on the control signals from the control unit 120, one end of the wire is fixed, and the tension of the wire is adjusted by winding or unwinding the wire. The wire drawn out from the winding part engages with (wraps around) the pulley of the connecting region of the waist frame 105 and the first frames 108Ra, 108La and the pulley of the connecting region of the first frames 108Ra, 108La and the second frames 108Rb, 108Lb, and the other end is fixed to the third frames 108Rc, 108Lc.

The power transmission mechanism is designed to limit the range of rotation of the connecting regions of the respective frames in correspondence with the range of motion of the monkey's femoral joint and knee joint so that the monkey's gait (repetitive pattern of the leg movement focused on timing) based on the monkey's leg anatomy will be substantially constant.

The motion transmission mechanism of the body-worn motion assist device 110 as the foregoing modified example is able to adjust the tension of the wire by driving the drive motor of the pair of left and right winding parts mounted on the waist frame 105, and use such tension in the walking motion of the right leg assist part 106R and the left leg assist part 106L.

(6-5) Target-Based Functional Improvement Evaluation Method

(6-5-1) Motor Function Improvement Evaluation Method

In this embodiment, when the monkey's spinal cord is damaged or ruptured (when the monkey's spinal cord is intentionally damaged or ruptured for an evaluation experiment), by implanting a sensor on the side of the nerve center (brain) that is above the damaged or ruptured area and detecting the biosignals (nerve action potentials) based on commands from the brain while causing the monkey with a spinal cord injury to walk on the treadmill 102, the monkey's walking motion is assisted.

In this embodiment also, without limitation the side that is above the damaged or ruptured area of the monkey's spinal cord, it is also possible to implant a potential detection sensor (electrode) on a side that is below the damaged or ruptured area of the monkey's spinal cord, and detect the biosignals (for example, bioelectric potential signals) that are fed back from the peripheral system to the central nervous system when the monkey engages in a walking motion. Moreover, a sensor for applying physical stimulation such as electrostimulation to the biotissues may also be provided in substitute for, or integrally with, the potential detection sensor.

(6-5-2) Physiological Function Improvement Evaluation Method

Furthermore, in addition to applying the functional improvement evaluation apparatus 100 of the present invention to the motor function improvement of monkeys, it may also be applied to the physiological function improvement of a bladder/excretory disorder or the like. In this embodiment also, in the same manner as the case of using a rat described in the foregoing embodiment, with a catheter (not shown) inserted into the monkey's bladder, the functional improvement of the bladder/excretory disorder is monitored, simultaneously with assisting the monkey's walking motion, based on the biosignals detected from the intended in vivo site (spinal cord, cranial nerve or the like) while causing the monkey to engage in a walking motion.

REFERENCE SIGNS LIST

1, 100 . . . functional improvement evaluation apparatus, 2, 101 . . . base, 3, 102 . . . treadmill, 4 . . . spherical rolling part, 5 . . . walking motion assist device, 7, 114 . . . walking belt, 10, 116 . . . relief device, 11, 118 . . . input unit, 12a, 12b, 109a, 109b . . . special-purpose shoes, 15, 130 . . . biosignal detection unit, 16, 122 . . . sensor, 17, 131 . . . control device, 18, 132 . . . joint angle detection unit, 19, 133 . . . centroid position detection unit, 20, 107 . . . motion transmission mechanism, 21, 123 . . . driving source, 30 . . . culture substrate, 31, 52 . . . nanofiber, 34, 40, 41, 42 . . . implant module, 50 . . . hollow nanofiber, 110 . . . body-worn motion assist device.

The invention claimed is:

1. A nerve cell culture apparatus, comprising:
   an implant module which is implanted in an intended in vivo site of a mammalian model animal, and the implant module places nerve cells and a guide member, which guides neurites of the nerve cells in an elongation direction, on a culture substrate;
   a potential detector which is radially mounted at a plurality of sites centering around the in vivo site, including at least a central side above the implant module, and detects each nerve action potential with reference to the in vivo site;
   a motion transmitter which is connected to a holding part for holding a foot of each leg of the model animal, and transmits the power of the driving source to the holding part so that the holding part swings at an approximate trajectory as a natural walking motion pattern of the model animal;
   a treadmill, which has a walking belt positioned to come into contact with the holding part, and causes the walking belt to move in a circular motion according to a rotation of rollers; and
   a controller, which causes a driving source to generate power according to an intent of the model animal and based on each of the nerve action potentials detected by the potential detector,
   wherein the controller controls the power of the driving source based on a swing angle of the holding part connected to the motion transmitter by determining a measured angle of a joint of the model animal based on the swing angle of the holding part, comparing the measured angle of the joint to stored reference powers to identify a task associated with movement of the model animal and autonomously controlling the driving source based on a stored assist pattern associated with the identified task while simultaneously examining a cell activity of the nerve cells based on a measurement result of changes in each of the nerve action potentials during the autonomous control of the driving source, and culturing nerve cells in the implant module implanted in the in vivo site of the model animal during the controlling a moving speed of the walking belt according to a walking motion of the model animal.

2. The nerve cell culture apparatus according to claim 1, further comprising:
   a biostimulation application unit which is provided integrally with the potential detector, and applies electrostimulation by way of a square wave current to the model animal based on signals from the controller,
   wherein the controller, while measuring an action potential that was reflected in response to the electrostimulation by the biostimulation application unit, controls a directivity of elongation of the nerve cells (32) by controlling a stimulation frequency of electrostimulation based on a relationship of the action potential and cell activity of the nerve cells.

3. The nerve cell culture apparatus according to claim 1, further comprising:
   a centroid position detection unit which is provided on the holding part for holding a foot of each leg of the model animal, and the centroid position detection unit detects a centroid position according to a walking motion of the model animal; and
   a relief device which lifts the model animal in a freely elevatable manner, and relieves a load on a foot of each leg of the model animal, and
   wherein the controller controls the relief by the relief device based on the centroid position of the model animal.

4. The nerve cell culture apparatus according to claim 1, wherein the motion transmitter includes an articulated link mechanism having at least 1 degree of freedom, and converts at least a part of a rotational motion of the driving source into at least pseudo linear motion.

5. The nerve cell culture apparatus according to claim 1, wherein the motion transmitter includes:
- a waist frame to be mounted on a waist of the model animal;
- first frames which are provided downward from a right side and a left side of the waist frame, respectively, and rotatably connected at a position corresponding to a hip joint of the model animal; and
- second frames which are provided downward from each of the first frames and rotatably connected at a position corresponding to a knee joint of the model animal,
- wherein an output of the driving source is transmitted to a connecting region of the waist frame and the first frame and a connecting region of the first frame and the second frame, respectively.

6. The nerve cell culture apparatus according to claim 1, wherein the controller compares a nerve action potential of an electrode disposed in the in vivo site of the model animal and a nerve action potential of a subcutaneous implanted electrode disposed on a muscle surface corresponding to the in vivo site, and estimates a restoration level of the in vivo site based on the comparison result.

* * * * *